(12) United States Patent
Stevens et al.

(10) Patent No.: US 8,784,856 B2
(45) Date of Patent: Jul. 22, 2014

(54) MEADOWFOAM-BASED BIOHERBICIDE PRODUCTS

(75) Inventors: Jan F. Stevens, Corvallis, OR (US);
Stephen Machado, Pendleton, OR (US);
Ralph Reed, Philomath, OR (US);
Michael S. Martinez, Salem, OR (US)

(73) Assignee: The State of Oregon Acting by and Through the State Board of Higher Education on Behalf of Oregon State University, Corvallis, OR (US)

( * ) Notice: Subject to any disclaimer, the term of this patent is extended or adjusted under 35 U.S.C. 154(b) by 854 days.

(21) Appl. No.: 12/664,984

(22) PCT Filed: Jul. 21, 2008

(86) PCT No.: PCT/US2008/070632
§ 371 (c)(1),
(2), (4) Date: Jul. 20, 2010

(87) PCT Pub. No.: WO2009/012485
PCT Pub. Date: Jan. 22, 2009

(65) Prior Publication Data
US 2010/0317518 A1 Dec. 16, 2010

Related U.S. Application Data

(60) Provisional application No. 60/961,323, filed on Jul. 19, 2007.

(51) Int. Cl.
*A01N 25/32* (2006.01)
*A01N 25/08* (2006.01)
*A01N 25/28* (2006.01)
*A01N 65/00* (2009.01)

(52) U.S. Cl.
CPC ............... *A01N 25/32* (2013.01); *A01N 25/28* (2013.01); *A01N 65/00* (2013.01)

USPC ...... 424/406; 424/94.1; 424/94.2; 424/94.61; 424/400; 424/405; 424/409; 424/410; 424/725; 424/755; 424/776; 426/47; 426/49; 426/52

(58) Field of Classification Search
None
See application file for complete search history.

(56) References Cited

U.S. PATENT DOCUMENTS 2,987,399 A * 6/1961 Goering ........................... 426/44
3,044,876 A * 7/1962 Goering ......................... 426/417

(Continued)

OTHER PUBLICATIONS

Z. Bialy et al., "Allelopathic potential of glucosinolates (mustard oil glycosides) and their degradation products against wheat", Plant and Soil, 129: 277-281 (1990).

(Continued)

*Primary Examiner* — Neil Levy
(74) *Attorney, Agent, or Firm* — Patrick J. Hagan; Dann, Dorfman, Herell and Skillman, P.C.

(57) ABSTRACT

Particular aspects provide methods for converting glucosinolate in a glucosinolate-containing plant material to glucosinolate breakdown products (GBPs), comprising: providing an amount of processed glucosinolate-containing plant material, the processed material being depleted of oil and glucosinolate converting enzyme activity by virtue of said processing; providing an amount of glucosinolate converting enzyme activity; mixing the processed material with the amount enzyme activity; hydrating the mixture; and incubating the hydrated mixture, wherein the glucosinolates are enzymatically converted to GBPs. Preferably, the processed plant material comprises a oilseed-derived seedmeal material (e.g., meadowfoam seedmeal) from which the oil has been removed by the processing (e.g., solvent extraction and/or heat treatment). In particular embodiments, the glucosinolate converting enzyme activity comprises at least one of a myrosinase activity and a nitrile-forming activity. Additional aspects provide low-fat compositions (e.g., herbicide, fungicide, insecticide, bacteriostatic or bactericidal, cosmetic, cosmeceutical or pharmaceutical) comprising GBPs derived from a glucosinolate-containing plant material.

53 Claims, 11 Drawing Sheets

(56) References Cited

U.S. PATENT DOCUMENTS

| | | |
|---|---|---|
| 6,436,450 B1 | 8/2002 | Omary et al. |
| 6,596,323 B1 | 7/2003 | Deuel |
| 7,105,190 B2 | 9/2006 | Ekanayake et al. |

OTHER PUBLICATIONS

Paul Brown et al., "Allelochemicals Products During Glucosinolate Degradation in Soil", J. Chem. Ecol., 17(10): 2021-2034 (1991).

S. Buskov et al., "Effects of Intact Glucosinolates and Products Produced from Glucosinolates in Myrosinase-Catalyzed Hydrolysis on the Potato Cyst Nematode (*Globodera rostochiensis* Cv. Wolf)", J. Agric. Food Chem., 50: 690-695 (2002).

Jim E. Dale, "Decline in Phytotoxicity of Benzyl Isothiocyanate Formulated as Granules", Weed Science, 34: 325-327 (1986).

Albena T. Dinkova-Kostova et al., "Protection against UV-light-induced skin carcinogenesis in SKH-1 high-risk mice by sulforaphane-containing broccoli sprout extracts", Cancer Letters, 240: 243-252 (2006).

Albena T. Dinkova-Kostova et al., "Induction of the Phase 2 Response in Mouse and Human Skin by Sulforaphane-containing Broccoli Sprout Extracts", Cancer Epidemiol. Biomarkers Prev., 16(4): 847-851 (2007).

Martin G. Ettlinger et al., "The Mustard Oil of *Limnanthes douglasii* Seed, m-Methoxybenzyl Isothiocyanate", J. Am. Chem. Soc., 78: 1952-1954 (1955).

Jed W. Fahey et al., "Sulforaphane inhibits extracellular, intracellular, and antibiotic-resistant strains of *Helicobacter pylori* and prevents benzo[a]pyrene-induced stomach tumors", PNAS, 99(11): 7610-7615 (2002).

Jed W. Fahey et al., "Broccoli sprouts: An exceptionally rich source of inducers of enzymes that protect against chemical carcinogens", Proc. Natl. Acad. Sci. USA, 94: 10367-10372 (1997).

Jed W. Fahey et al., "The chemical diversity and distribution of glucosinolates and isothiocyanates among plants", Phytochemistry, 56: 5-51 (2001).

Xiangqun Gao et al., "Powerful and prolonged protection of human retinal pigment epithelial cells, keratinocytes, and mouse leukemia cells against oxidative damage:" The indirect antioxidant effects of sulforaphane, PNAS, 98(26) 15221-15226 (2001).

Xenophon Hasapis et al., "Benzylglucosinolate Degradation in Heat-Treated *Lepidium sativum* Seeds and Detection of a Thiocyanate-Forming Factor", Phytochemistry, 21: 1009-1013 (1982).

S. Jain, Domestication of *Limnanthes* (Meadowfoam) as a New Oil Crop, Plant Domestication by Induced Mutation: Proceedings of an Advisory Group Meeting on the Possible Use of Mutation Breeding for Rapid Domestication of New Crop Plants, Vienna, Austria, 1986; pp. 121-134.

Steven J. Knapp et al., "Breeding Advances and Germplasm Resources in Meadowfoam: A Novel Very Long Chain Oilseed", In Perspectives on new crops and new uses, J. Janick, ed., ASHS Press, Alexandria, VA, pp. 225-233 (1999).

Xian Li et al., "Purification and characterization of myrosinase from horseradish (*Armoracia rusticana*) roots", Plant Physiology and Biochemistry, 43: 503-511 (2005).

Stephen Machado et al., "Allelopathic Potential of Various Plant Species on Downy Brome: Implications for Weed Control in Wheat Production", Agronomy Journal, 99: 127-132 (2007).

M. Mari et al., "In vitro activity of glucosinolate-derived isothiocyanates against postharvest fruit pathogens", Ann. Appl. Biol., 123: 155-164 (1993).

Charles T. Mason, Jr., "A Systematic Study of the Genus *Limnanthes* R. Br.", University of California: Berkeley, pp. 455-512 (1952).

R.W. Miller et al., "Search for New Industrial Oils. VIII. The Genus *Limnanthes*", J. Am. Oil Chem. Soc., 41: 167-196 (1964).

Mark J. Potter et al., "Suppressive Impact of Glucosinolates in *Brassica* Vegetative Tissues on Root Lesion Nematode *Pratylenchus neglectus*", J. Chem. Ecol., 24(1): 67-80 (1998).

Hans J. Prochaska et al., "Rapid detection of inducers of enzymes that protect against carcinogens", Proc. Natl. Acad. Sci. USA, 89: 2394-2398 (1992).

Paul Talalay et al., "Phytochemicals from Cruciferous Plants Protect against Cancer by Modulating Carcinogen Metabolism", In American Institute for Cancer Research 11th Annual Research Conference on Diet, Nutrition and Cancer, 3027S-3033S (2001).

Paul Talalay et al., "Sulforaphane mobilizes cellular defenses that protect skin against damage by UV radiation", PNAS, 104(44): 17500-17505 (2007).

Steven F. Vaughn et al., "Herbicidal activity of glucosinolate-containing seedmeals", Weed Science, 54(4): 743-748 (2006).

Steven F. Vaughn et al., "Isolation and Identification of (3-Methoxyphenyl)acetonitrile as a Phytotoxin from Meadowfoam (*Limnanthes alba*) Seedmeal", J. Chem. Ecol., 22(10): 1939-1949 (1996).

Livy Williams, III et al., "Toxicity of Allyl Isothiocyanate-Amended Soil to *Limonius californicus* (Mann.) (Coleoptera: Elateridae) Wireworms", J. Chem. Ecol., 19(6): 1033-1046 (1993).

* cited by examiner

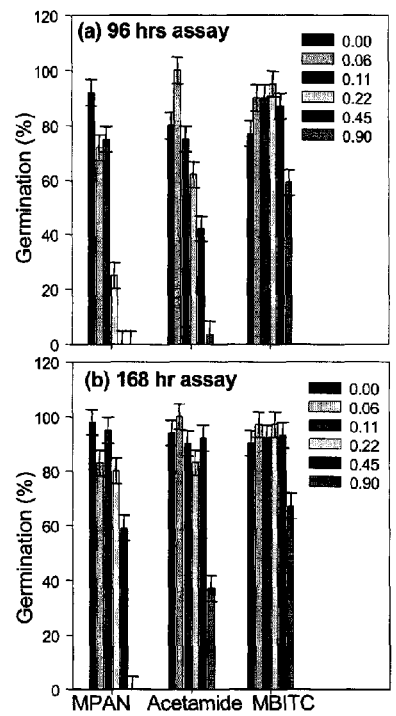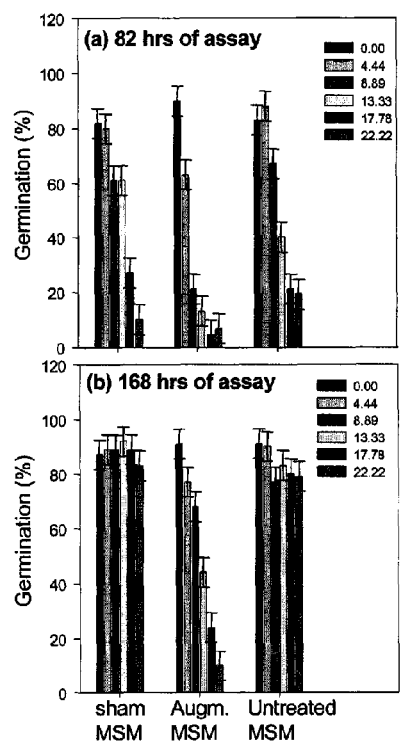
FIGURE 8 FIGURE 9

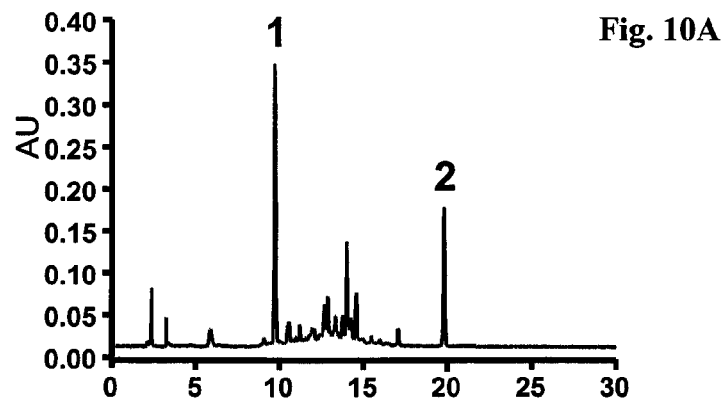
Fig. 10A
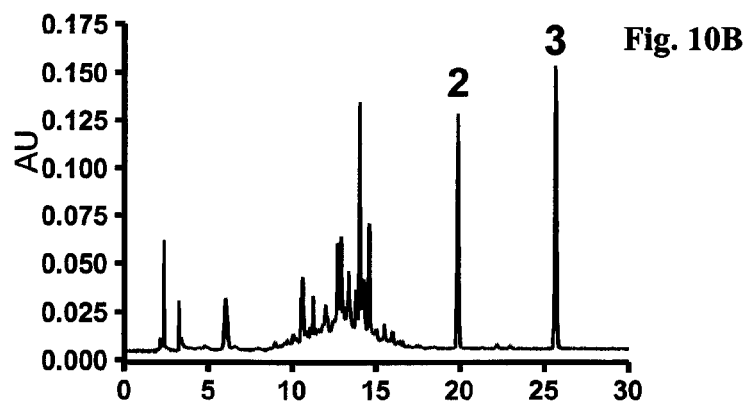
Fig. 10B
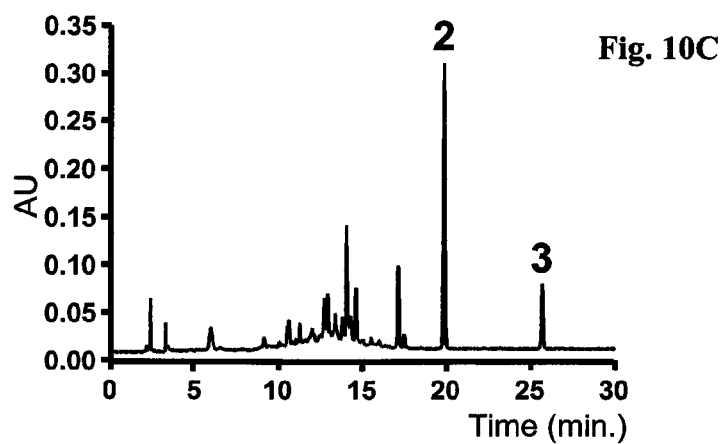
Fig. 10C
FIGURE 10

MEADOWFOAM-BASED BIOHERBICIDE PRODUCTS

CROSS-REFERENCE TO RELATED APPLICATIONS

This application is the U.S. National Stage of International Application No. PCT/US2008/070632, filed Jul. 21, 2008, which claims benefit of U.S. Provisional Application No. 60/961,323, filed Jul. 19, 2007, the entire disclosures of which are incorporated by reference herein.

STATEMENT REGARDING FEDERALLY SPONSORED RESEARCH

This work was partially funded by the United States Department of Agriculture/Cooperative State Research, Education, and Extension Service grant number 2005-34407-15670, and the United States government has, therefore, certain rights to the present invention.

FIELD OF THE INVENTION

Particular aspects relate generally to herbicides and, in particular embodiments, to meadowfoam-based bioherbicide compositions and methods for making and using the same. Additional aspects relate to methods for converting glucosinolate in a glucosinolate-containing plant material to glucosinolate breakdown products (GBPs) to provide compositions (e.g., herbicide, fungicide, insecticide, bacteriostatic or bactericidal, cosmetic, cosmeceutical or pharmaceutical), including low-fat concentrates, comprising GBPs, and methods of making and using same.

BACKGROUND

Organic agricultural market. Declining markets and prices for conventionally grown products, coupled with concerns of ecological, environmental, and health, are factors motivating growers to pursue 'organic' markets, which are growing at a rate of over 20% per year. There are, however, problems and challenges inherent to organic farming systems where conventional use of synthetic pesticides, herbicides and fertilizers is not tolerated. For example, while weeds may be controlled by tillage, tillage is not only labor intensive, but also exposes the soil to wind and water erosion thus depleting organic matter. Moreover, the acreages of organic crops have been limited by the cost of mechanical weed control methods.

Accordingly, the use of natural products as herbicides has the potential to significantly leverage financial resources by reducing tillage operations and labor requirements, so that acreages of organic crops can be increased.

Glucosinolates, and Glucosinolate-Containing Plant Materials.

Many plant species are known to have alleopathic effects (negative and positive) on other plant species, and this property can be exploited for weed control purposes. Over 500 plant species contain glucosinolates, of which 16 glucosinolate families are known. While there is a large variety of glucosinolates, there is a common common glycosinolate substrate core structure (e.g., glucose residue linked by a thioglucoside bond to an amino acid derivative) (formula 1), wherein the "R" group is varied between and among different plants.

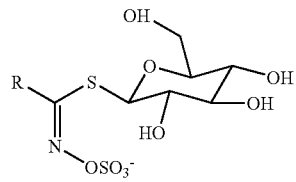

formula 1

Based on this core structure, the release of the alleopathic compounds from glucosinolates is primarily mediated by a β-thioglucosidases enzyme called myrosinase, explaining, at least in part, the herbicidal (allelopathic; germination inhibitory) effects of many glucosinolate-containing plants (e.g., meadowfoam (*Limnanthes alba*) and plant seed materials Meadowfoam.

Meadowfoam (*Limnanthes alba*) is an exemplary glucosinolate-containing plant material. Meadowfoam is a herbaceous winter-spring annual grown as a commercial oilseed crop primarily for its seed oil comprising unique C20 and C22 fatty acids (e.g., for the lubricants, plastics, cosmetic and pharmaceutical industries). Meadowfoam seedmeal (MSM) is a spent seed byproduct of the solvent extraction process used to remove meadowfoam oil from meadowfoam seed. Meadowfoam seeds are also a rich source of glucolimnanthin (GLN), a glucosinolate that releases a toxic isothiocyanate upon crushing of the seeds. This release of toxic compounds, mediated by a thioglucosidase enzyme called myrosinase, explains, at least in part, the known herbicidal (allelopathic; germination inhibitory) effects of Meadowfoam seeds. The industrial-scale oil heat-extraction process destroys any enzyme activity in the seeds. Thus, while the spent seed material, meadowfoam seedmeal (MSM), contains 2-4% glucosinolate, the MSM has relatively little allelopathic (germination inhibitory) activity absent its conversion to alleopathic compounds. MSM, therefore, aside from its potential use as an exogenous plant growth substance (see, e.g., U.S. Pat. No. 6,596,323), has been generally regarded as a problematic waste product of the seed oil extraction process—at least until the present invention.

There is therefore, a pronounced need in the art for novel, cost effective natural herbicides that can be used in the context of organic farming and gardening. There is a pronounced need in the art for novel, cost effective natural herbicides based on processed glucosinolate-containing plant material, such as the exemplary MSM.

Other Markets and Utilities for Glucosinolate Breakdown Products.

As discussed herein below, in addition to herbicidal utility, glucosinolate-derived compounds have been used as fungicides, insecticides, bacteriostatic or bactericidal agents, cosmetic additives, and cosmeceutical and/or pharmaceutical agents (e.g., cancer, chemoprotectant, anti-aging, bacteriostatic, bactericidal, treatment and/or prevention of ulcers, treatment and/or prevention of gastritis, treatment of skin disorders including but not limited to eczema, facial eczema, dermatitis, external ulcers, welts, rashes, insect bites, allergic reactions and other irritations, burns, wounds, psoriasis, acneiform eruptions, dryness, dry skin, irritation, skin atrophy, secondary infections and the like).

There is therefore, a pronounced need in the art for novel, cost effective natural fungicides, insecticides, bacteriostatic or bactericidal agents, cosmetic additives, and cosmeceutical and/or pharmaceutical agents.

There is a pronounced need in the art for novel, cost effective methods to provide such products from processed glucosinolate-containing plant materials, such as the exemplary MSM.

SUMMARY OF EXEMPLARY EMBODIMENTS

Particular aspects provide novel bioherbicides, along with methods for making same from processed glucosinolate-containing plant materials.

Particular specific exemplary embodiments provide meadowfoam-based bioherbicide compositions and methods for making and using the same.

Additional aspects provide methods for converting glucosinolate in a glucosinolate-containing plant material to glucosinolate breakdown products (GBPs) to provide compositions (e.g., herbicide, fungicide, insecticide, bacteriostatic or bactericidal, cosmetic, cosmeceutical or pharmaceutical), including low-fat concentrates, comprising GBPs, and methods of making and using same.

Particular aspects provide surprisingly effective methods for converting glucosinolate (e.g., glucolimnanthin) in processed plant materials (e.g, enzyme-inactivated spent seeds, such as meadowfoam seed meal, MSM) into alleopathic compounds (e.g., the corresponding isothiocyanate, nitriles, etc.) by treating the processed plant materials with relatively small or minute amounts of exogenously provided enzyme-active plant materials (e.g., seed materials). In particular aspects, the treated processed plant material products comprises enhanced levels of alleopathic compounds (e.g., the corresponding isothiocyanate, nitriles, etc.), and have substantially greater herbicidal activity than the regular, untreated processed plant material (e.g., MSM, etc.)

Additional aspects provide identification of a novel nitrile-forming enzyme in meadowfoam seeds that converts glucolimnanthin into the corresponding glucolimnanthin-nitrile, shown herein to have greater herbicidal activity than the glucolimnanthin-isothiocyanate.

In additional aspects, therefore, the treated MSM product comprises enhanced levels of the corresponding glucolimnanthin-nitrile, and has substantially greater herbicidal activity than the regular, untreated MSM.

In preferred aspects, the treated MSM product comprises enhanced levels of both the corresponding glucolimnanthin-isothiocyanate and the glucolimnanthin-nitrile, and has substantially greater herbicidal activity than the regular, untreated MSM.

Additional aspects provide methods for selectively converting glucolimnanthin into the corresponding glucolimnanthin-nitrile using the naturally-occurring nitrile-forming enzyme in meadowfoam seeds.

According to various aspects, therefore, fresh, enzyme-active meadowfoam seeds comprise, in addition to an active thioglucosidase enzyme (myrosinase), a novel nitrile-forming enzyme, and preferred aspects provide methods for making potent meadowfoam-based bioherbicides by converting the glucolimnanthin in MSM to glucolimnanthin-isothiocyanate, and/or by converting, or selectively converting the glucolimnanthin in MSM into glucolimnanthin-nitrile, the methods comprising treating MSM with relatively small or minute amounts of fresh, enzyme-active meadowfoam seed material, comprising at least one of the active thioglucosidase enzyme (myrosinase), and the novel nitrile-forming enzyme. According to additional aspects, the source of the active thioglucosidase enzyme (myrosinase), and the novel nitrile-forming enzyme may be other than meadowfoam, provided that the conversion of the MSM glucolimnanthin to the corresponding glucolimnanthin-isothiocyanate and/or glucolimnanthin-nitrile is afforded.

Particular aspects provide methods for converting glucosinolate in a glucosinolate-containing plant material to glucosinolate breakdown products (GBPs), comprising: providing an amount of processed glucosinolate-containing plant material, the processed plant material being depleted of oil and glucosinolate converting enzyme activity by virtue of said processing; providing an amount of glucosinolate converting enzyme activity; contacting or mixing the processed glucosinolate-containing plant material with the amount of glucosinolate converting enzyme activity; hydrating the mixture; and incubating the hydrated mixture, wherein the glucosinolates in the processed glucosinolate-containing plant material are enzymatically converted to glucosinolate breakdown products (GBPs). In certain aspects, the processed glucosinolate-containing plant material comprises a oilseed-derived seed-meal material from which the oil has been removed by the processing, and wherein the processing comprises at least one of solvent extraction and heat treatment. In particular embodiments, the glucosinolate converting enzyme activity comprises at least one of a myrosinase activity and a nitrile-forming activity. In certain embodiments, the glucosinolate converting enzyme activity comprises that of a heterologous plant relative to the processed glucosinolate-containing plant material. In particular aspects, providing the glucosinolate converting enzyme activity comprises providing a plant material having glucosinolate converting enzyme activity. In certain aspects, the plant material having glucosinolate converting enzyme activity comprises seed material of a seed oil plant. In particular embodiments, the amount of plant material having glucosinolate converting enzyme activity is present in an amount less than 2 wt %, less than 5 wt %, or less than 10 wt %, relative to the amount of processed glucosinolate-containing plant material. In certain embodiments, the glucosinolate breakdown products (GBPs), comprise at least one of a glucosinolate-derived isothiocyanate, a glucosinolate-derived nitrile and an acetamide derivative of a glucosinolate-derived nitrile. In particular aspects, incubating the hydrated mixture is in the presence of a co-factor or agent that promotes formation of the glucosinolate-derived nitrile or acetamide derivative of a glucosinolate-derived nitrile, relative to formation of the glucosinolate-derived isothiocyante. In certain aspects, the co-factor or agent comprises a metal ion. In particular embodiments, the metal is at least one selected from the group consisting of $Fe^{2+}$, $Zn^{2+}$, $Ca^{2+}$, $Mg^{2+}$, $Cu^{2+}$, and $Mn^{2+}$. In particular aspects, the methods further comprising drying or freeze drying the incubated hydrated mixture. In certain aspects, at least one of the processed glucosinolate-containing plant material and the glucosinolate converting enzyme activity comprises material from at least one plant selected from the group consisting of: Crambe (*Crambe abysinnica*); Black Mustard; Yellow Mustard (*Sinapis alba*); Oriental Mustard (*Brassica juncea*); Broccoli (*Brassica oleracea italica*); Rapeseed (*Brassica napus*); Meadowfoam (*Limnanthes alba*), Radish (*Raphanus sativus*); Wasabi (*Wasabia japonica*); Horseradish (*Cochlearia Armoracia*); Cauliflower (*Brassica oleracea*); Garden cress (*Lepidium sativum*); Watercress (*Nasturtium officinalis*); and Papaya (*Carica papaya*). In particular embodiments, at least one of the processed glucosinolate-containing plant material and the glucosinolate converting enzyme activity comprises material from Meadowfoam (*Limnanthes alba*). In certain aspects, at least one of the processed glucosinolate-containing plant material and the glucosinolate converting enzyme activity comprises material from the genus *Brassicas*.

1. Additional aspects provide a method for providing a low-fat composition comprising glucosinolate breakdown products (GBPs) derived from a glucosinolate-containing plant material, comprising: providing an amount of processed glucosinolate-containing plant material, the processed plant material being depleted of oil glucosinolate converting enzyme activity by virtue of said processing; providing an amount of glucosinolate converting enzyme activity; contacting or mixing the processed glucosinolate-containing plant material with the amount of glucosinolate converting enzyme activity; hydrating the mixture; and incubating the hydrated mixture, wherein the glucosinolates in the processed glucosinolate-containing plant material are enzymatically converted to glucosinolate breakdown products (GBPs) to provide for a low-fat composition comprising glucosinolate breakdown products (GBPs) derived from a glucosinolate-containing plant material. In particular aspects, the method further comprises drying or freeze drying the incubated hydrated mixture to provide for a dried composition comprising glucosinolate breakdown products (GBPs). In certain aspects, the method further comprises grinding, crushing, pulverizing, mincing, milling or otherwise breaking up the dried or freeze dried material to provide a dried or freeze dried material having increased surface area. In particular embodiments, the method further comprises extracting the dried or freeze dried material having increased surface area with a solvent to provide for partitioning of one or more glucosinolate breakdown products (GBPs) from the dried or freeze dried material into the solvent. In certain embodiments, the method further comprises segregating the extract-bearing solvent from the extracted dried or freeze dried material, and desolventizing the extract-bearing solvent to provide an extract composition comprising glucosinolate breakdown products (GBPs). Particular embodiments further comprises desolventizing the extracted dried or freeze dried material to provide a re-extracted plant material depleted of oil, glucosinolates and glucosinolate breakdown products (GBPs). In certain aspects, the processed glucosinolate-containing plant material comprises a, oilseed-derived seedmeal material from which the oil has been removed by the processing, and wherein the processing comprises at least one of solvent extraction and heat treatment. In particular embodiments, the low-fat composition comprises a GBP to fat (FFA plus TAG) ratio, in terms of wt %, in the range of about 1:1 to about 1:3. In certain embodiments, the extract composition comprises a GBP to fat (FFA plus TAG) ratio, in terms of wt %, in the range of about 1:1 to about 1:3. In particular aspects, the glucosinolate converting enzyme activity comprises at least one of a myrosinase activity and a nitrile-forming activity. In particular aspects, the glucosinolate converting enzyme activity comprises that of a heterologous plant relative to the processed glucosinolate-containing plant material. In certain aspects, providing the glucosinolate converting enzyme activity comprises providing a plant material having glucosinolate converting enzyme activity. In certain embodiments, the plant material having glucosinolate converting enzyme activity comprises seed material of a seed oil plant. In particular embodiments, the amount of plant material having glucosinolate converting enzyme activity is present in an amount less than 2 wt %, less than 5 wt %, or less than 10 wt %, relative to the amount of processed glucosinolate-containing plant material. In certain aspects, the glucosinolate breakdown products (GBPs), comprise at least one of a glucosinolate-derived isothiocyante, a glucosinolate-derived nitrile and an acetamide derivative of a glucosinolate-derived nitrile. In particular preferred aspects, incubating the hydrated mixture is in the presence of a co-factor or agent that promotes formation of the glucosinolate-derived nitrile or acetamide derivative of a glucosinolate-derived nitrile, relative to formation of the glucosinolate-derived isothiocyante. In certain preferred embodiments, the co-factor or agent comprises a metal ion and/or ascorbic acid (or ascorbate). Preferably, the metal is at least one selected from the group consisting of $Fe^{2+}$, $Zn^{2+}$, $Ca^{2+}$, $Mg^{2+}$, $Cu^{2+}$, and $Mn^{2+}$. In particular aspects, at least one of the processed glucosinolate-containing plant material and the glucosinolate converting enzyme activity comprises material from at least one plant selected from the group consisting of *Crambe* (*Crambe abysinnica*); Black Mustard; Yellow Mustard (*Sinapis alba*); Oriental Mustard (*Brassica juncea*); Broccoli (*Brassica oleracea italica*); Rapeseed (*Brassica napus*); Meadowfoam (*Limnanthes alba*), Radish (*Raphanus sativus*); Wasabi (*Wasabia japonica*); Horseradish (*Cochlearia Armoracia*); Cauliflower; Garden cress (*Lepidium sativum*); Watercress (*Nasturtium officinalis*); and Papaya (*Carica papaya*). In certain aspects, at least one of the processed glucosinolate-containing plant material and the glucosinolate converting enzyme activity comprises material from Meadowfoam (*Limnanthes alba*). In particular embodiments, at least one of the processed glucosinolate-containing plant material and the glucosinolate converting enzyme activity comprises material from the genus *Brassicas*.

Additional aspects, provide a low-fat composition comprising glucosinolate breakdown products (GBPs) derived from a glucosinolate-containing plant material, wherein the low-fat composition comprises a GBP to fat (FFA plus TAG) ratio, in terms of wt %, in the range of about 1:1 to about 1:3. In certain embodiments, the composition is an extract composition, comprising a GBP to fat (FFA plus TAG) ratio, in terms of wt %, in the range of about 1:1 to about 1:3.

Yet additional aspects provide a low-fat composition comprising glucosinolate breakdown products (GBPs) derived from a glucosinolate-containing plant material, the composition made according to the above methods. In certain embodiments, the composition comprises an extract comprising glucosinolate breakdown products (GBPs) according to the disclosed methods.

Further aspects provide an herbicide or allelopathic composition, a fungicide, an insecticide, a bacteriostatic or bactericidal composition, or a cosmetic or cosmeceutical composition, comprising at least one of the disclosed compositions. In particular aspects, the cosmetic or cosmeceutical composition is one selected from the group consisting of skin creams and ointments, moisturizing creams and ointments, sun screen compositions, anti-aging compositions, anti-oxidant compositions, lotions, skin creams, night creams, make-up, after sun products, and eye creams.

Yet further aspects provide a pharmaceutical composition, comprising at least one of the disclosed compositions along with a pharmaceutically acceptable excipient or carrier. In particular aspects, the pharmaceutical composition is at least one selected from the group consisting of treatment and/or prevention of cancer, anti-aging, bacteriostatic, bactericidal, treatment and/or prevention of ulcers, and treatment and/or prevention of gastritis.

Additional aspects provide a method of treatment of a disorder, comprising administration to a subject in need thereof, a therapeutically effective amount of a pharmaceutical composition according the present invention, wherein the disorder is at least one selected from the group consisting of cancer, aging, bacterial infection, ulcers, gastritis, skin disorders, eczema, facial eczema, dermatitis, external ulcers, welts, rashes, insect bites, allergic reactions and other irritations, burns, wounds, psoriasis, acneiform eruptions, dryness, dry skin, irritation, skin atrophy, and secondary infections.

Additional aspects provide a method of agricultural weed control, comprising administration of at least one of the disclosed composition.

Yet additional aspects, provide a method for providing a low-fat composition comprising a glucosinolate-containing plant material, comprising: providing an amount of processed glucosinolate-containing plant material, the processed plant material being depleted of oil and glucosinolate converting enzyme activity by virtue of said processing; providing an amount of glucosinolate converting enzyme activity; and mixing the processed glucosinolate-containing plant material with the amount of glucosinolate converting enzyme activity to provide a low-fat composition comprising a processed glucosinolate-containing plant material. In particular aspects, the method comprises drying or freeze drying the incubated hydrated mixture to provide for a dried low-fat composition comprising glucosinolate breakdown products (GBPs). In certain aspects, the method comprises grinding, crushing, pulverizing, mincing, milling or otherwise breaking up the dried or freeze dried material to provide a dried or freeze dried low-fat material having increased surface area. In particular embodiments, the method comprises pelletizing the low-fat composition comprising a glucosinolate-containing plant material. In certain aspects, the processed glucosinolate-containing plant material comprises a, oilseed-derived seedmeal material from which the oil has been removed by the processing, and wherein the processing comprises at least one of solvent extraction and heat treatment. In particular embodiments, the glucosinolate converting enzyme activity comprises at least one of a myrosinase activity and a nitrile-forming activity. In certain aspects, the glucosinolate converting enzyme activity comprises that of a heterologous plant relative to the processed glucosinolate-containing plant material. In particular embodiments, providing the glucosinolate converting enzyme activity comprises providing a plant material having glucosinolate converting enzyme activity. In certain embodiments, the plant material having glucosinolate converting enzyme activity comprises seed material of a seed oil plant. In particular aspects, the plant material having glucosinolate converting enzyme activity is present in an amount less than 2 wt %, less than 5 wt %, or less than 10 wt %, relative to the amount of processed glucosinolate-containing plant material. In certain aspects, the glucosinolate breakdown products (GBPs), comprise at least one of a glucosinolate-derived isothiocyante, a glucosinolate-derived nitrile and an acetamide derivative of a glucosinolate-derived nitrile. In certain embodiments, the method further comprises providing a co-factor or agent that promotes formation of the glucosinolate-derived nitrile or acetamide derivative of a glucosinolate-derived nitrile, relative to formation of the glucosinolate-derived isothiocyante, and mixing the co-factor or agent with the processed glucosinolate-containing plant material with the amount of glucosinolate converting enzyme activity. In particular preferred aspects, the co-factor or agent comprises a metal ion. Preferably, the metal is at least one selected from the group consisting of $Fe^{2+}$, $Zn^{2+}$, $Ca^{2+}$, $Mg^{2+}$, $Cu^{2+}$, and $Mn^{2+}$. In particular aspects, at least one of the processed glucosinolate-containing plant material and the glucosinolate converting enzyme activity comprises material from at least one plant selected from the group consisting of: Crambe (*Crambe abysinnica*); Black Mustard; Yellow Mustard (*Sinapis alba*); Oriental Mustard (*Brassica juncea*); Broccoli (*Brassica oleracea italica*); Rapeseed (*Brassica napus*); Meadowfoam (*Limnanthes alba*), Radish (*Raphanus sativus*); Wasabi (*Wasabia japonica*); Horseradish (*Cochlearia Armoracia*); Cauliflower; Garden cress (*Lepidium sativum*); Watercress (*Nasturtium officinalis*); and Papaya (*Carica papaya*). In certain embodiments, at least one of the processed glucosinolate-containing plant material and the glucosinolate converting enzyme activity comprises material from Meadowfoam (*Limnanthes alba*). In particular aspects, at least one of the processed glucosinolate-containing plant material and the glucosinolate converting enzyme activity comprises material from the genus *Brassicas*.

Further aspects provide a low-fat composition made according to any of the above-described methods. Yet further aspects provide a herbicide or allelopathic composition comprising said low-fat compositions.

Additional aspects provide a method of agricultural weed control, comprising administration of a low-fat composition according to the present invention.

BRIEF DESCRIPTION OF THE DRAWINGS

FIGS. 8A and 8B show, according to particular exemplary embodiments, the effect of Glucolimnanthin degradation products (MPAN, Acetamide and MBITC) on downy brome germination after 82 hours (FIG. 8A) and 168 hours (FIG. 8B) of assay. The rates of application are in mg test compound per gram soil.

FIGS. 9A and 9B show, according to particular exemplary embodiments, the effect of MSM augmented with enzyme-active meadowfoam seed ("Augm. MSM"), sham MSM and untreated MSM on downy brome germination after 82 hours (FIG. 9A) and 168 hours (FIG. 9B) of assay. The rates of application are in mg MSM per gram soil.

FIGS. 10A, 10B and 10C show HPLC analysis of untreated meal (panel A), meal treated with 1% myrosinase-active meadowfoam seeds (panel B), and meal incubated with a 10 mM solution of $FeSO_4$ in the presence of 1% myrosinase-active meadowfoam seeds (panel C). The UV trace was recorded at 274 nm.

DETAILED DESCRIPTION OF EXEMPLARY EMBODIMENTS

Figure 1:
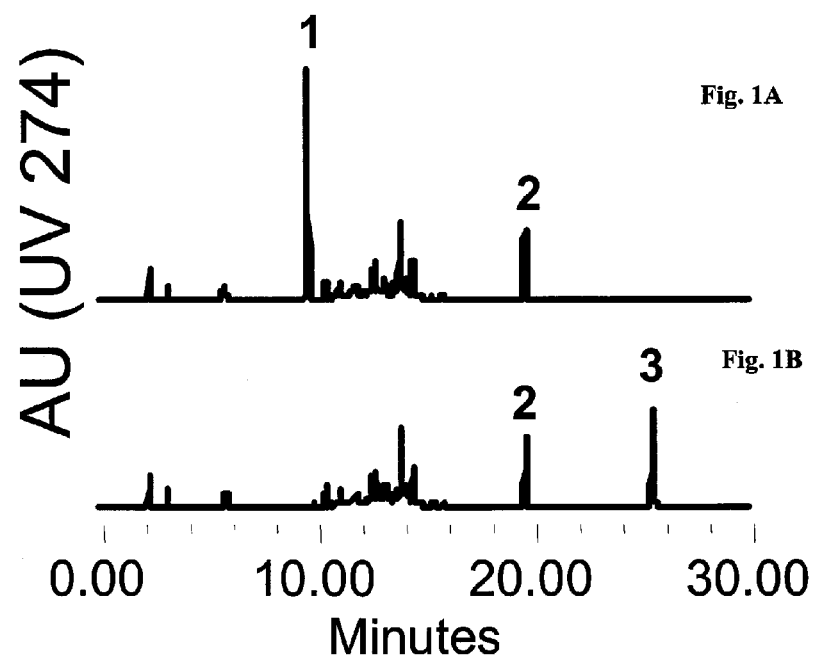
FIGS. 1A and 1B show, according to particular exemplary embodiments, HPLC analysis of MeOH—$H_2O$ extracts of meadowfoam seedmeal ("MSM") pre-treated with a 3-fold amount of water by weight (FIG. 1A), and MSM inoculated with 1% myrosinase-active meadowfoam seeds and pre-treated with water (FIG. 1B). Key to peaks: "1"=GLN (glucolimnanthin), "2"=MPAN (3-methoxyphenyl-acetonitrile), and "3"=MBITC (3-methoxybenzyl isothiocyanate).

Composition and method aspects of the present invention provide for novel and cost effective natural herbicides (bioherbicides) using processed, glucosinolate-containing plant material (e.g., meadowfoam (Limnanthes alba) seed meal (MSM). The inventive natural herbicides provide alternatives to synthetic agrochemicals, where the natural herbicides are less toxic to humans and their natural environment.

Additional aspects provide methods for converting glucosinolate in a glucosinolate-containing plant material to glucosinolate breakdown products (GBPs) to provide compositions (e.g., herbicide, fungicide, insecticide, bacteriostatic or bactericidal, cosmetic, cosmeceutical or pharmaceutical), including low-fat concentrates, comprising GBPs, and methods of making and using same.

In particular aspects, the natural herbicides have substantial utility as allelopathic (germination inhibitory) compositions that can be used in farming (e.g., organic farming) for many crops, including but not limited to growth production of organic wheat (Triticum aestivum L.) and other organic cropping systems.

Exemplary aspects of the invention have been demonstrated in context of processed, glucosinolate-containing plant material (e.g., MSM) from meadowfoam. The main economic value of meadowfoam lies in the seed oil which is a rich source of C20 and C22 fatty acids for the cosmetic and pharmaceutical industry. Applicants have conceived and reduced to practice as described herein, that the spent seed material, meadowfoam seedmeal (MSM), which contains 2-4% glucosinolate (glucolimnanthin), could be exploited to cost effectively provide glucolimnanthin-derived products having allelopathic (germination inhibitory) activities suitable to provide for effective weed control in, for example, organic farming systems (e.g., to facilitate organic wheat and other organic crop production).

In particular aspects, Applicants initially obtained data showed that MSM inhibits germination of cheatgrass (Bromus tectorum), the dominant grass weed in Oregon's wheat producing areas, and further data also surprisingly demonstrated that enzyme-induced degradation of glucosinolate in MSM yields an MSM product with enhanced herbicidal activity.

Particular specific exemplary aspects of the present invention, therefore, provide for isolation, identification, and determination of the herbicidal activity of phytochemicals in MSM and products derived from MSM.

Additional aspects provide for enhancing the herbicidal activity of processed, glucosinolate-containing plant material (e.g., MSM) by converting inactive glucosinolate into active degradation products by 'inoculating' the processed, glucosinolate-containing plant material with enzyme-active plant materials (e.g., with ground meadowfoam seeds, and/or other sources of glucosinolate (e.g., glucolimnanthin)-converting enzymes).

Yet additional aspects provide for enhancing the herbicidal activity of processed, glucosinolate-containing plant material (e.g., MSM) by altering the processing conditions in a factory (e.g., by reducing or eliminating steps that irreversibly inactivate glucosinolate (glucolimnanthin)-converting enzymes).

Further aspects provide for the use of processed, glucosinolate-containing plant material (e.g., MSM) and enhanced processed, glucosinolate-containing plant material products as bioherbicides in organic farming, including but not limited to dryland organic wheat farming, where the herbicidal activity of the enhanced processed, glucosinolate-containing plant material, and the untreated processed, glucosinolate-containing plant material products can be implemented in open field plots.

The idea of using meadowfoam seed material as a biocatalytic composition for conversion of inactive GLN into products with allelopathic activity in glucosinolate-containing processed plant material (e.g., MSM, etc.) is novel and has not previously been suggested or explored. The result is surprising in view of the processing steps typically used for oil extraction (e.g., mechanical disruption, heat-treatments, solvent extractions, desiccation, etc.), which are employed at least in part to intentionally inactivate myrosinase and otherwise preclude conversion of glucosinolates (i.e., so as not to contaminate the oil with glucosinolate breakdown products), and would be expected to not only inactivate enzymatic activities, but also to alter the context of the glucosinolate substrate per se, thus compromising the biochemical availability of the post-processed glucosinolate (e.g., GLN) to act as productive substrate for enzymes introduced post-processing. This is particularly true in view of the fact that the naturally occurring enzymatic conversion of glucosinolate substrate occurs in the context of plant oils (e.g., approximately 30 wt %, or greater, in seeds of oilseed plants). Unexpectedly, however, aspects of the present invention provide compositions and methods for producing MSM products with enhanced levels of either MBITC and/or MPAN by treating oil-depleted MSM with relatively minute amounts of meadowfoam seed material comprising glucosinolate-converting activities, and optionally adding or removing specific cofactors (e.g., $Fe^{2+}$ (e.g., 10 mM ferrous sulphate), ascorbic acid, ascorbate, etc.).

Exemplary Preferred Embodiments

Particular aspects provide methods for converting glucosinolate in a glucosinolate-containing plant material to glucosinolate breakdown products (GBPs), comprising: providing an amount of processed glucosinolate-containing plant material, the processed material being depleted of oil and glucosinolate converting enzyme activity by virtue of said processing; providing an amount of glucosinolate converting enzyme activity; contacting or mixing the processed material with the amount enzyme activity; hydrating the mixture; and incubating the hydrated mixture, wherein the glucosinolates are enzymatically converted to GBPs. Preferably, the processed plant material comprises a oilseed-derived seedmeal material (e.g., meadowfoam seedmeal) from which the oil has been removed by the processing (e.g., solvent extraction and/or heat treatment). In particular embodiments, the glucosinolate converting enzyme activity comprises at least one of a myrosinase activity and a nitrile-forming activity. Additional aspects provide low-fat compositions (e.g., herbicide, fungicide, insecticide, bacteriostatic or bactericidal, cosmetic, cosmeceutical or pharmaceutical) comprising GBPs derived from a glucosinolate-containing plant material.

Yet additional aspects, provide a method for providing a low-fat composition comprising a glucosinolate-containing plant material, comprising: providing an amount of processed glucosinolate-containing plant material, the processed plant material being depleted of oil and glucosinolate converting enzyme activity by virtue of said processing; providing an amount of glucosinolate converting enzyme activity; and mixing the processed glucosinolate-containing plant material with the amount of glucosinolate converting enzyme activity to provide a low-fat composition comprising a processed glucosinolate-containing plant material.

Additional aspects provide a method for providing a low-fat composition comprising glucosinolate breakdown products (GBPs) derived from a glucosinolate-containing plant material, comprising use of the inventive methods.

Additional aspects, provide low-fat compositions comprising glucosinolate breakdown products (GBPs) derived from a glucosinolate-containing plant material, wherein the low-fat composition comprises a GBP to fat (FFA plus TAG) ratio, in terms of wt %, in the range of about 1:1 to about 1:3, including where such low-fat compositions are made by the exemplary methods. In certain embodiments, the compositions are extract compositions, comprising a GBP to fat (FFA plus TAG) ratio, in terms of wt %, in the range of about 1:1 to about 1:3, including where such low-fat extract compositions are made by the exemplary methods.

Further aspects provide an herbicide or allelopathic composition, a fungicide, an insecticide, a bacteriostatic or bactericidal composition, or a cosmetic or cosmeceutical composition, comprising at least one of the disclosed compositions. In particular aspects, the cosmetic or cosmeceutical composition is one selected from the group consisting of skin creams and ointments, moisturizing creams and ointments, sun screen compositions, anti-aging compositions, anti-oxidant compositions, lotions, skin creams, night creams, make-up, after sun products, and eye creams.

Yet further aspects provide a pharmaceutical composition, comprising at least one of the disclosed compositions along with a pharmaceutically acceptable excipient or carrier. In particular aspects, the pharmaceutical composition is at least one selected from the group consisting of treatment and/or prevention of cancer, anti-aging, bacteriostatic, bactericidal, treatment and/or prevention of ulcers, and treatment and/or prevention of gastritis.

Additional aspects provide a method of treatment of a disorder, comprising administration to a subject in need thereof, a therapeutically effective amount of a pharmaceutical composition according the present invention, wherein the disorder is at least one selected from the group consisting of cancer, aging, bacterial infection, ulcers, gastritis, skin disorders, eczema, facial eczema, dermatitis, external ulcers, welts, rashes, insect bites, allergic reactions and other irritations, burns, wounds, psoriasis, acneiform eruptions, dryness, dry skin, irritation, skin atrophy, and secondary infections.

Additional aspects provide a method of agricultural weed control, comprising administration of at least one of the disclosed composition.

Conversion of the Meadowfoam Glucosinolate, Glucolimnanthin ("GLN,"), into the Corresponding Isothiocyanate ("MBITC"), and/or the Nitrile ("MPAN"):

Many plant species are known to have allelopathic effects (negative and positive) on other plant species, and this property can be exploited for weed control purposes.

The white meadowfoam (*Limnanthes alba* Hartw. ex Benth., Limnanthaceae) is native to southern Oregon and northern California (2, 3). Several cultivars have emerged from a meadowfoam breeding program at Oregon State University (4). The species is cultivated in the Willamette valley of western Oregon for the seed oil which is rich in unusual C20 and C22 fatty acids (5). The oil has commercial value as an ingredient of personal care products and cosmetics.

According to particular aspects of the present invention, meadowfoam contains the glucosinolate, glucolimnanthin ("GLN," in Scheme 1 below), whose degradation products have the potential to inhibit seed germination of other plant species. Glucosinolates comprise a group of secondary plant metabolites that release allelopathic phytochemicals in postmortem plant tissues through myrosinase-mediated cleavage of glucose residues, a key step that sets the stage for further degradation. In the case of glucolimnanthin, cleavage of the glucose and sulfate residues gives rise to the formation of substituted 3-methoxybenzyl analogs with isothiocyanate, nitrile, and amide functional groups (Scheme 1). Although it has been shown that the glucolimnanthin degradation product, 3-methoxyphenyl-acetonitrile (MPAN), contains seed germination inhibitory effects against velvetleaf (*Abutilon theophrasti*) and wheat, the nature and extent to which other phytochemicals in meadowfoam contribute to allelopathic activity was, until now, largely unknown. Applicants conceived that the allelopathic activity of MSM is due to GLN degradation products, and therefore investigated chemical and enzymatic ways to degrade GLN in MSM.

More specifically, according to preferred aspects, the spent seed material (meal) (MSM) can be used as a bioherbicide due to the presence of allelochemicals. With reference to Scheme 1, below, the meal contains the glucosinolate, glucolimnanthin 1 (6), and 3-methoxyphenylacetonitrile (2), a known allelochemical (7) formed by heat-induced degradation of 1 during the oil extraction process. 3-Methoxybenzyl-isothiocyanate (3) is the main product of myrosinase-mediated degradation of the glucosinolate 1 in crushed seeds, but 3 is virtually absent in meal due to heat-inactivation of myrosinase as part the oil extraction process. The heat treatment is necessary to prevent contamination of the oil with non-polar breakdown products of 1. As disclosed herein, the conversion of 1 into the allelochemicals 2 and 3 (7) in enzyme-inactive meal was investigated by making use of active enzymes present in meadowfoam seeds. Applicants demonstrate that enzyme-treated meal products contain greater amounts of 2 or 3 and show greater inhibitory activity in a seed germination assay, compared to untreated meadowfoam seed meal. Scheme 1 shows, according to particular aspects, degradation of the glucosinolate, glucolimnanthin 1 ("GLN"), into the isothiocyanate 3 ("MBITC"), and the nitrile 2 ("MPAN"). The conversion of GLN into MBITC is mediated by the thioglucosidase, myrosinase.

According to particular aspects of the present invention, the conversion of GLN into MPAN can be achieved enzymatically in the absence of presence or transition metal ions.

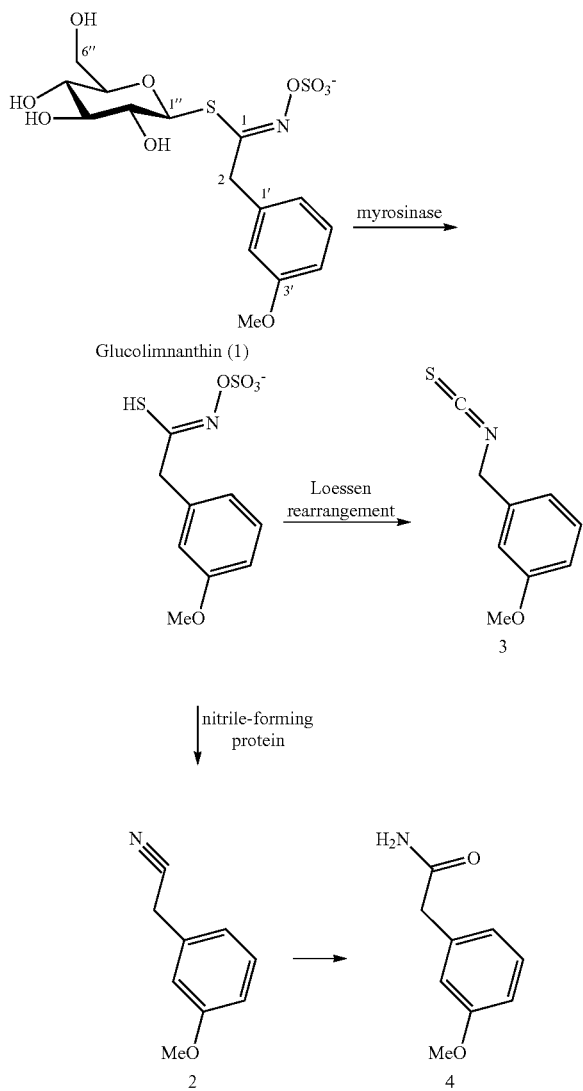

Working EXAMPLE 1, herein below, describes Applicant's analytical methods, based on HPLC for the detection and quantitation of the glucosinolate glucolimnanthin ("GLN"), the corresponding isothiocyanate ("MBITC"), and the corresponding nitrile ("MPAN") in meadowfoam products (meadowfoam seedmeal; "MSM"). Bulk MSM, (provided by Natural Plant Products, Inc., Oregon) contained up to 4% GLN, up to 0.6% MPAN, and virtually no MBITC. Meadowfoam (*Limnanthes alba*) seed material, obtained from the Department of Crop and Soil Science at Oregon State University (OSU), was found to contain about 3% GLN after heat-treatment to inactivate myrosinase.

As described in working EXAMPLE 2, herein below, Applicants conceived that the allelopathic activity of MSM is due to GLN degradation products, and therefore investigated chemical and enzymatic ways to degrade GLN in MSM. The commercial extraction of oil from meadowfoam seeds involves a heating step in order to avoid contamination of the oil with the apolar degradation products of GLN, primarily MPAN and MBITC.

Significantly, Applicants reasoned that such a heating step likely inactivates enzymes in the MSM, including those that might be involved with GLN degradation, and further conceived and confirmed that 'inoculation' (e.g., treatment) of myrosinase-inactive MSM with small amounts of ground, myrosinase-active meadowfoam seed (e.g., 1%) resulted in a significant conversion of GLN into MBITC when the inoculation mixture was brought into contact with water (compare panels A and B in FIG. 1). Specifically, peak 3 of panel B in FIG. 1 corresponds to the presence of MBITC, resulting from the 'inoculation.'

According to additional aspects, as shown in FIGS. 2A, 2B and 2C of working EXAMPLE 3, 'augmented' MSM can be prepared from myrosinase-inactive MSM by 'inoculation' with small amounts of ground, myrosinase-active meadowfoam seed (e.g., 1%), and pretreatment with water. Moreover, as seen from the germination inhibition results of FIG. 9, the augmented MSM showed increased potency as a germination inhibitor as compared to untreated MSM and sham-treated MSM. The results of the germination experiments (FIGS. 8 and 9) are thus consistent with the formation of a substantial amount of MBITC from GLN, as shown in FIG. 2C.

Figure 3:
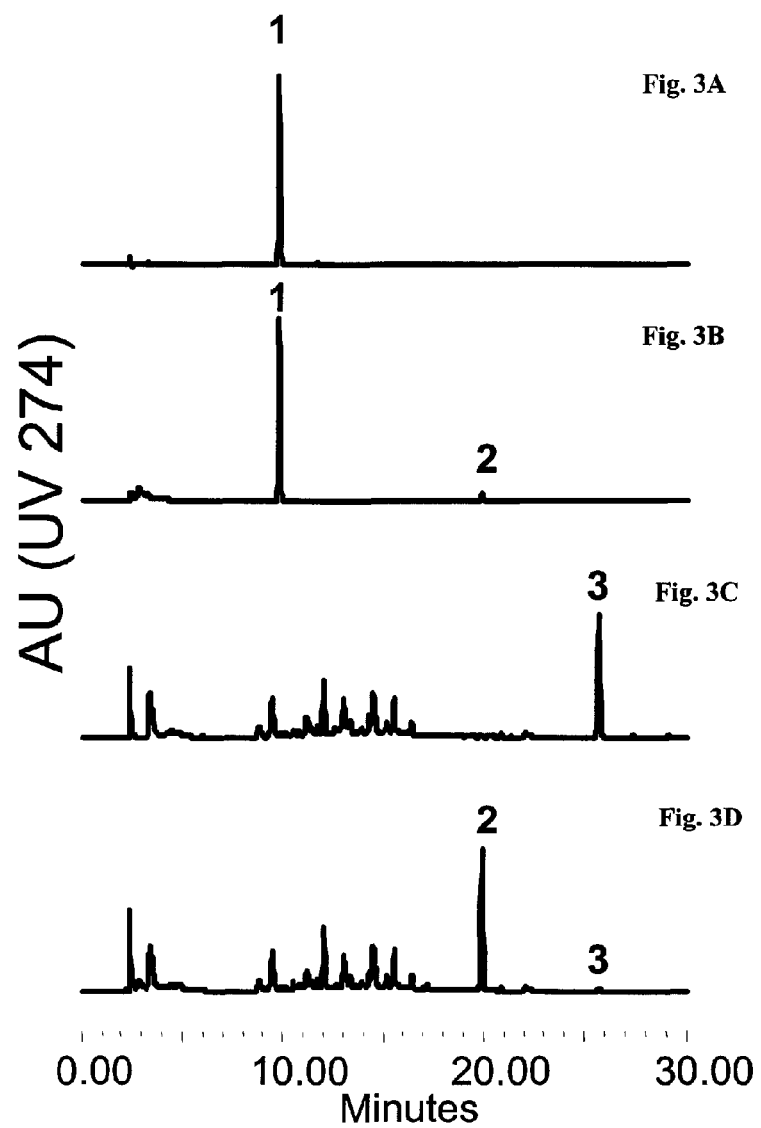
FIGS. 3A, 3B, 3C and 3D show, according to particular exemplary embodiments, HPLC analysis of GLN (1 mM, FIG. 3a); 1 mM GLN in the presence of 10 mM $Fe^{2+}$ (FIG. 3B); 1 mM GLN incubated with broccoli juice without addition of $Fe^{2+}$ (FIG. 3C); and 1 mM GLN incubated with broccoli juice in the presence of 10 mM $Fe^{2+}$ (FIG. 3D). The HPLC conditions and peak numbering are the same as in FIGS. 1A and 1B.

In further aspects, as described in working EXAMPLE 4, Applicants have not only determined that the conversion of meadowfoam-derived GLN to MBITC can be affected by heterologous myronsinase enzymes (e.g., from broccoli), but have also determined that the addition of $Fe^{2+}$ to the reaction preferentially promotes nitrile formation from the meadowfoam-derived GLN. Specifically, Applicants conceived that the herbicidal activity of MSM products might be increased by preferentially directing enzymatic conversion of GLN to the corresponding nitrile (MPAN). In this regard, Applicants incubated GLN (1 mM) with juice prepared from broccoli sprouts ('broccoli juice'), and discovered that GLN is converted into the corresponding isothiocyanate (MBITC), indicating that heterologous broccoli myrosinase accepts meadowfoam GLN as a substrate (compare panels A and C in FIG. 3). Interestingly, when the experiment was repeated in the presence of $Fe^{2+}$ (e.g., 10 mM ferrous sulphate), GLN was mainly converted into MPAN while very little MBITC was formed (FIG. 3D), indicating that the addition of $Fe^{2+}$ activated a nitrile-forming protein (e.g., enzyme) that also accepts the heterologous GLN as a substrate. Very little conversion of GLN was observed in the presence of 10 mM $Fe^{2+}$ alone (FIG. 3B), further confirming the presence of a nitrile-forming protein (e.g., enzyme) in broccoli juice.

This experiment demonstrates, according to particular embodiments, that enzymatic conversion of meadowfoam-derived GLN can be directed to MPAN. These results raised the question as to whether meadowfoam seeds contain a nitrile-forming enzyme that could be exploited to produce an MSM product with enhanced levels of MPAN. Applicants have determined that this, in fact, is the case.

Specifically, as shown herein below under working EXAMPLE 5, while incubation of MSM with a solution of $FeSO_4$ (10 mM) had no significant effect on the composition and very little extra MPAN was formed (FIG. 4, panel A), when MSM was 'inoculated' with myrosinase-active meadowfoam seeds and the mixture incubated with a 10 mM solution of $FeSO_4$, a substantial amount of MPAN was formed (e.g., compare panels A and B in FIG. 4), indicating that meadowfoam seeds contain an $Fe^{2+}$-dependent nitrile-forming enzyme in addition to myrosinase.

Figure 5:
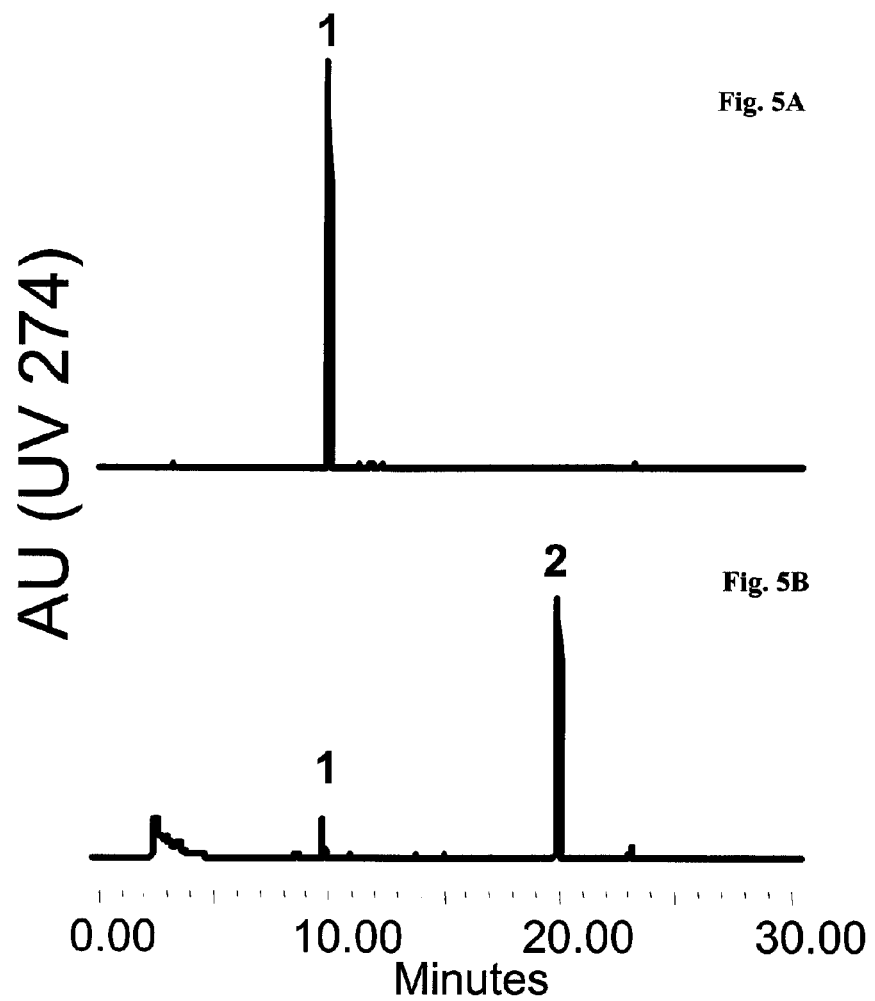
FIGS. 5A and 5B show, according to particular exemplary embodiments, HPLC analysis of an aqueous solution of GLN (1 mM) after heating for 60 minutes at 90° C. in the absence (FIG. 5A), and in the presence (FIG. 5B) of 10 mM $FeSO_4$. The HPLC conditions and peak numbering are the same as in FIGS. 1A and 1B.

In further aspects, described under working EXAMPLE 6 below, Applicants investigated the effect of heating on the degradation of GLN in the absence and presence of $Fe^{2+}$ ions, and demonstrated that heating an aqueous solution of meadowfoam-derived GLN in the presence of $Fe^{2+}$ causes formation of MPAN in about 90% yield. Specifically, as shown in FIG. 5, heating (e.g., 60 minutes at 90° C.) of an aqueous solution of GLN containing 10 mM $FeSO_4$ causes formation of MPAN in about 90% yield, whereas incubation of 1 mM GLN with 10 mM $FeSO_4$ at room temperature did not result in significant degradation of GLN (see FIG. 3B).

Therefore, additional aspects of the present invention provide methods for producing MSM products with enhanced levels of MPAN comprising heating in the presence of $Fe^{2+}$ (e.g., 10 mM ferrous sulphate).

Taken together, the data shown under working EXAMPLES 1 through 6, show that Applicants have not only developed tools to isolate, identify and quantify phytochemicals in MSM on a laboratory scale, but have also developed methods applicable to large-scale production of MSM products with enhanced levels of MBITC and MPAN, which were identified as herbicidal compounds in seed germination experiments.

According to additional aspects, therefore, an MSM product with enhanced levels of MPAN can be produced by treating MSM with myrosinase-active meadowfoam seed material in the presence of $Fe^{2+}$ (e.g., 10 mM ferrous sulphate). According to particular aspects, meadowfoam seeds are a rich source of glucolimnanthin, a glucosinolate capable of giving rise to one or more alleopathic compounds (e.g., the corresponding isothiocyanate) upon crushing of the seeds. This release of the alleopathic compounds is enzyme mediated, and in certain aspects is mediated by a thioglucosidase enzyme called myrosinase, explaining, at least in part, the herbicidal (allelopathic; germination inhibitory) effects of meadowfoam seeds.

According to additional aspects, the industrial-scale oil extraction process destroys any enzyme activity in the seeds and in the meadowfoam seedmeal (MSM), the spent seed byproduct of the heat distillation process used to extract meadowfoam oil from meadowfoam seed.

Particular aspects, therefore, provide surprisingly effective methods for converting glucosinolate (glucolimnanthin) in enzyme-inactivated spent seeds (meadowfoam seed meal, MSM) into alleopathic compounds (e.g., the corresponding isothiocyanate) by treating MSM with minute amounts of fresh, enzyme-active seeds. In particular aspects, the treated MSM product comprises enhanced levels of alleopathic compounds (e.g., the corresponding isothiocyanate), and has substantially greater herbicidal activity than the regular, untreated MSM.

Additional aspects provide identification of a novel nitrile-forming enzyme in meadowfoam seeds that converts glucolimnanthin into the corresponding glucolimnanthin-nitrile, shown herein to have greater herbicidal activity than the glucolimnanthin-isothiocyanate. In additional aspects, therefore, the treated MSM product comprises enhanced levels of the corresponding glucolimnanthin-nitrile, and has substantially greater herbicidal activity than the regular, untreated MSM. In preferred aspects, therefore, the treated MSM product comprises enhanced levels of both the corresponding glucolimnanthin-isothiocyanate and the glucolimnanthin-nitrile, and has substantially greater herbicidal activity than the regular, untreated MSM.

Therefore, according to particular aspects, fresh, enzyme-active meadowfoam seeds comprise, in addition to an active thioglucosidase enzyme (myrosinase), a novel nitrile-forming enzyme, and preferred aspects provide methods for making potent meadowfoam-based bioherbicides by converting the glucolimnanthin in MSM to glucolimnanthin-isothiocyanate, and/or by converting, or selectively converting, glucolimnanthin into glucolimnanthin-nitrile, the methods comprising treating MSM with minute amounts of fresh, enzyme-active meadowfoam seeds, comprising at least one of the active thioglucosidase enzyme (myrosinase), and the novel nitrile-forming enzyme. According to additional aspects, the source of the active thioglucosidase enzyme (myrosinase), and the novel nitrile-forming enzyme may be other than meadowfoam, provided that the conversion of the MSM glucolimnanthin to the corresponding glucolimnanthin-isothiocyanate and/or glucolimnanthin-nitrile is afforded.

Additional aspects of the present invention provide methods for producing glucosinolate-containing plant material products (e.g., MSM products) with enhanced levels of MPAN comprising heating (e.g., 60 minutes at 90° C., in the presence of $Fe^{2+}$ (e.g., 10 mM ferrous sulphate).

Significantly, the nature of the methods provide for implementation on an industrial-scale for production of augmented MSM with little additional costs.

Extraction and Concentration Process Embodiments:

Applicants' disclosed technology provides novel ways to convert glucosinolate (GS) glucosinolate-containing plant materials to their more biologically active glucosinolate breakdown products (GBPs) such as isothiocyanates and nitriles described herein. As described in exemplary embodiments herein, 'fermented' meal (e.g., MSM) is manufactured by combining meal with ground seed (unheated), moistening (e.g., with water or a solution of iron sulfate), holding, and freeze drying. Aside from agricultural utilities, GBPs are highly desired compounds in a number of industries including: pharmacy, veterinary, and cosmetics.

In additional aspects therefore, as discussed in more detail under EXAMPLE 9 (Exemplary extraction techniques for removing glucosinolate breakdown products from fermented seedmeals in more concentrated forms), regrinding and extraction techniques are employed to link the fermentation procedure to an extraction procedure to generate a liquid extract containing GBPs. This provides for production of more purified and concentrated compositions.

Additional aspects thus provide extraction techniques that allow for extraction of the GBPs from the treated glucosinolate-containing plant materials, and concentration of the GBPs in a liquid form. A liquid format offers many additional formulation options, compared to those of solid, powder forms of treated glucosinolate-containing plant materials (e.g., treated MSM). As will be appreciated by one of skill in the relevant art, a variety of commercially viable extraction systems are available for this purpose, including continuous operation extractor, and batch operation extractors. Any of these may be applied to the extraction in question with varying degrees of success.

Batch extraction systems are generally composed of a sealed vessel with a perforated screen at the bottom and solvent spray head at the top. The material to be extracted is inserted into the vessel and rests above the screen. Solvent is then added to the system and flows down through the material. Typically, solvent is recirculated for a prescribed amount of time. The solvent/solvate combination is then separated and desolventized leaving the extract.

Continuous extraction systems are the standard in the vegetable oil industry. The two major manufacturers are Crown Iron Works (Minneapolis, Minn.) and DeSmet (Zaventem, Belgium). While the engineering designs are significantly different, the basic principle is the same. Briefly, the material to be extracted is placed into a vessel and flows through the unit while being rinsed with solvent. Some units are composed of distinct extraction stages where pure solvent is added during the final stage and then moves through to the first stage. Thus in the first stage, the material is extracted with solvent already containing extract. The process, known as a counter-current system, maximizes solvent performance. Particular continuous extraction systems are designed to handle high loads of "fines." Fermented and reground meal is a representative example of fines. In particularly preferred aspects of the present invention, a Crown Model IV extractor (designed to extract fines) provides an effective route of extraction.

Extraction Solvents.

According to further aspects, a variety of solvents may be used, with the particular choice of extraction solvent affecting the efficiency or degree of success. Exemplary, standard solvents in the industry include hexane and ethanol, and either or both may be used in practice of the disclosed methods. Additional examples include the use of methanol, which is less expensive than ethanol, and acetone. In particular preferred aspects, acetone is used, because it extracts a lower content of phospholipids (PLs), which are components of seed meals that may precipitate from the resulting extract. According to additional aspects, the solvent is removed after extraction.

Projected Composition of Concentrated Extracts:

As disclosed herein, meadowfoam seedmeal is approximately 4% glucosinolates, and 3% triglyceride oil by weight. Assuming 100% conversion of the glucosinolates to GBPs during fermentation, this allows for approximately 1.5% of extractable nitriles or isothiocyanates in the matrix. These represent the primary extractables in the matrix, so the extract will typically be composed of GPBs and meadowfoam oil. Depending on the amount of oil extraction (i.e., dilution), the GBP content will typically range from 20-60%, more typically 33-50%, with the balance primarily vegetable oil.

Delivery Considerations with Respect to Concentrated Extracts:

The extract, as described above, is considered a concentrate, allowing for dilution to a convenient dose concentration. Considering the broad range of industries in which GBPs can be used, concentrates provide convenient form (e.g. for sale and therapeutic delivery).

Isothiocyanates are known to react with proteins, and therefore consideration should be given to shielding the extract from such interactions in any formulation (e.g., in a personal care product or possibly a veterinary products). In particular aspects, such shielding this would be to incorporate the extract into a liposome or nanosomal delivery system; for example, having a hydrophobic core to dissolve the oil soluble GBPs, and a hydrophilic exterior to allow dispersion, dissolution, or emulsification in aqueous systems. Therapeutic application, for example, of such an emulsion causes the liposome/nanosome to break and the compound to be deposited on the target substrate. This is a very common method of delivering bioactive, but fragile components, in cosmetics and personal care products. Additional information on delivery and dosing follows below.

Low-Fat Compositions and Extracts Comprising Glucosinolate Breakdown Products (GBPs):

As known in the art, oilseeds have a high fat content, primarily in the form of free fatty acids (FFAs) and triacylglycerols (TAGs). Therefore, prior art methods for obtaining glucosinolate breakdown products (GBPs) comprising extraction or removal of GBPs from oilseed material has produced GBP-containing compositions that are high in fat (FFA plus TAGs) content due to co-extraction or co-removal of fat with the GBPs.

Significantly therefore, aspects of the present invention that comprise obtaining GBPs from processed glucosinolate-containing plant material, wherein the processed plant material is depleted of oil, provide, for the time, methods to obtain relatively concentrated, low-fat GBP-containing compositions and extracts.

For example, typical meadowfoam seed has a glucosinolate content (in the form of glucolimnanthin (GLN)) of about 3%, and an oil content of 30% (primarily as TAGs with about 0.5% in the form of FFA). The GLN content, therefore, in terms of GBPs would correspond to about 1.1 to 1.3 wt % in the seed. Assuming 100% conversion of GLN to GBPs, and conservatively assuming that only 29% of seed weight is extracted or removed as oil from the seed along with the GBPs, the ratio of GBP material to fat (FFA plus TAG) would be about 1.2:29, or greater, providing compositions wherein the GBPs are a relatively minor (e.g., almost a contaminant) component of the GBP-containing composition, rather than a major component of a GBP concentrate. Likewise, for other typical oilseeds (e.g., *Brassica*-type oilseeds, such as broccoli, mustard, canola, rape, etc.), which typically comprise glucosinolate loads not exceeding about 5%, and typically further comprising oil contents equal to or greater than that of meadowfoam.

By contrast, typical processed (oil removed or extracted) meadowfoam seedmeal (MSM) has a residual fat content (oil; primarily TAG with small amounts of FFA) of no more than about 1 or 2 wt %, or about 1 to 4 wt %, with a glucosinolate content of about 4 wt % (essentially all in the form of GLN). Assuming 100% conversion of GLN to the corresponding isothiocyanate (MBITC) and/or the nitrile (MPAN), and given the molecular weights of GLN, MBITC and MPAN as 422 g/mol, 179 g/mol and 147 g/mol, respectively, conversion of GLN to MPAN would provide for a 35 wt % GBP yield (i.e., =147/422), and conversion to MBITC would provide for a 42 wt % GBP yield. Given a 4 wt % GLN load in the processed MSM, the augmented MSM according to the present invention would have a GBP level of about 1.4 to 1.7 wt %. Therefore, augmented MSM compositions according to the present invention have a ratio of GBP material to fat (FFA plus TAG) of about 1.5:2 on a wt % basis. Moreover, in terms of compositions derived by extraction of augmented MSM (reasonably assuming that the GBPs and residual oil represent the primary extractables, and assuming 100% extraction of both), the composition of the inventive extracts approaches a GBP to fat (FFA plus TAG) ratio of 1:1 on a wt % basis. Conservatively, assuming that augmented MSM contains only 1.5% GBPs by weight (rather than 4 wt %), the extract would have a GBP to fat (FFA plus TAG) ratio of about 1.5:2 on a wt % basis. Likewise with respect to augmented SM and extracts obtainable from other oilseed types using Applicants' methods.

Therefore, aspects of the present invention provide, for the first time, methods to obtain relatively low-fat GBP-containing compositions and extracts. For example, the inventive GBP-containing augmented seedmeal SM compositions (e.g., augmented MSM) typically have a GBP to fat (FFA plus TAG) ratio, in terms of wt %, of about 1.5:2, and the inventive extract compositions (e.g., derived by extraction of the augmented MSM as described herein) typically have a GBP to fat (FFA plus TAG) ratio, in terms of wt %, in the range of about 1:1 to about 1:3, and more typically about 1.5:2 (compared with prior art ratios of about 1.2:29 or greater, in terms of wt %, as described above).

Therefore, the present inventive methods represent a substantial improvement over the prior art with respect to obtaining relatively concentrated, low-fat GBP-containing compositions and extracts comprising GPBs derived from glucosinolate-containing oilseed plant materials.

Agricultural Products Comprising Extracted GBPs:

According to particular aspects, the extracts are deliverable in typical agricultural products. Most active ingredients in pesticides, for example, are oil soluble compounds and are emulsified using surfactant systems well known in the industry. Besides allowing convenient delivery via liquid application, these surfactant systems could allow for more efficient application of the active principle and thus improve the economics.

General Applicability of the Methods to Glucosinolate-Containing Plant Materials:

Glucosinolates are converted into their corresponding isothiocyanates and other products by myrosinase, a β-thioglucosidase. Applicants' technology represents a novel way to convert glucosinolates in spent meal (e.g., MSM), where glucosinolates are present in a wide variety of plants. Over 500 plant species contain glucosinolates, of which sixteen families of dicotylendonous angiosperms are known. As will be appreciated by those of skill in the art, using routine methods in view of the present teachings, numerous other glucosinolate-containing plant materials feedstocks will have utility used for this technology. As described in EXAMPLE 8 below, the inventive methods are broadly applicable to 'glucosinolate-containing plant materials' (e.g., Brassicas).

In preferred aspects, the glucosinolate-containing plant materials comprises material from genus Brassicas. In certain preferred aspects, the glucosinolate-containing plant materials (and the glucosinolate content) comprises material from at least one of the material group consisting of: Crambe (Crambe abysinnica, e.g., 2-hydroxybut-3-enyl ITC); Black Mustard; Yellow Mustard (Sinapis alba, e.g., p-hydroxybenzyl glucosinolate; Oriental Mustard (Brassica juncea, 2-propenyl glucosinolate (aka sinigrin, which degrades to allyl ITC); Broccoli (Brassica oleracea italica, sulforaphane (4-methylsufinylbutyl ITC), glucoraphanin (parent glucosinolate)); Rapeseed (Brassica napus, 3-butenyl ITC); Meadowfoam, Radish (Raphanus sativus, 4-methylthio-3-butenyl ITC); Wasabi (Wasabia japonica, 4-methylthio-3-butenyl ITC); Horseradish (Cochlearia Armoracia, 2-phenylethyl ITC); Cauliflower (sulforaphane (4-methylsufinylbutyl ITC), glucoraphanin (parent glucosinolate)); Garden cress (Lepidium sativum, benzyl ITC); Watercress (Nasturtium officinalis, 2-phenylethyl ITC); and Papaya (Carica papaya, benzyl ITC).

Glucosinolates are β-thioglucoside N-hydroxysulfates [also known as (Z)-(or cis)-N-hydroximinosulfate esters or S-glucopyranosyl thiohydroximates], with a side chain (R) and a sulfur-linked β-D-glucopyranose moiety.

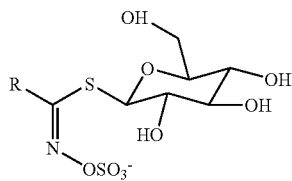

The most extensively studied glucosinolates are the aliphatic, 1-methylthioalkyl, aromatic and heterocyclic (e.g. indole) glucosinolates, typified by those found in the Brassica vegetables. Glucosinolate side chains, however, are characterized by a wide variety of chemical structures. The most numerous glucosinolates are those containing either straight or branched carbon chains. Many of these compounds also contain double bonds (olefins), hydroxyl or carbonyl groups, or sulfur linkages in various oxidation states. The largest single group (one-third of all glucosinolates) contain a sulfur atom in various states of oxidation (e.g. methyl-thioalkyl-, methylsulfinylalkyl-, or methylsulfonylalkyl). Another small group of benzyl glucosinolates have an additional sugar moiety, rhamnose or arabinose, in glycosidic linkage to the aromatic ring. EXAMPLE 8 lists exemplary glucosinolate-containing plant materials according to the present invention.

A comprehensive review of glucosinolate content in many plant species is provided by Fahey et al., Phytochemistry 56:5-51, 2001, which in incorporated herein by reference (see Tables 1 and 2, and FIG. 1 of Fahey et al. for comprehensive listing and structure). Fahey et al., describe glucosinolates (beta-thioglucoside-N-hydroxysulfates) present in sixteen families of dicotylendonous angiosperms, and describes fungicidal, bactericidal, nematocidal and allelopathic properties, along with cancer chemoprotective attributes. The antibacterial activities of glucosinolates/isothiocyanates have been known for decades, whereas the anti-cancer and chemoprotective effects have been more recently documented.

Use of Homologous or Heterologous Myrosinase:

Myrosinase.

According to additional aspects, Applicants have determined that the conversion of, for example, meadowfoam seedmeal (MSM) GLN to MBITC can be affected by heterologous myronsinase enzymes (e.g., from broccoli). Therefore, not only are the presently disclosed methods applicable to a broad variety of glucosinolate (e.g., GLN)-containing materials, but the source of the added myrosinase can be heterologous, and may be added as a purified enzyme preparation, or as a myrosinase-containing plant material (e.g., myrosinase-containing seeds, such as meadowfoam seeds). In addition to plant myrosinase, myrosinase is known to occur in fungus, and bacteria, such the myrosinase for use in the present invention may be fugal-derived or bacteria-derived. Various forms of myrosinase exist, and the glucosinolate-degrading enzyme myrosinase in Brassicaceae is, for example, encoded by a gene family. Many myrosinase proteins have been cloned and sequenced, and their respective sequence information is available in the GenBank database (see also EXAMPLE 8 below, and Table 2 thereof).

Herbicidal, Alleopathic Utilities; Inhibition of Seed Germination:

As described under working EXAMPLE 7 herein below, Applicants determined that GLN is not the active principle component of MSM with respect to herbicidal (anti-germination) activity. Therefore, Applicants investigated the effects of the GLN degradation products on downy brome seed germination (FIG. 8). Despite literature reports claiming that glucosinolate-derived isothiocyanates have allelopathic activity, Applicants found that MPAN and its acetamide analog, 2-(3-methoxyphenyl)acetamide, were more active as seed germination inhibitors than MBITC (FIG. 8).

Applicants, therefore, investigated the effect of GLN degradation in MSM on downy brome seed germination. As described under working EXAMPLE 7, and as shown in FIG. 9, augmented MSM showed greater inhibitory effects on seed germination than sham-treated MSM or untreated MSM.

Applicants' data indicates that MSM would completely inhibit the germination of downy brome if applied to the soil at the rate of 1500 kg ha$^{-1}$ (FIG. 1). At this rate, about 900 ha can be treated (e.g., twice the area under organic farming in Oregon (405 ha)). By contrast, and according to aspects of the present invention, producing augmented MSM as described herein, will substantially increase the efficacy of the MSM such that more fields can be treated using the available MSM supply. According to additional aspects, even a competitive advantage at early stages of growth may be sufficient to provide for satisfactory crops (e.g., wheat yields), such that it is not necessary to completely inhibit germination, thus effectively further extending the acreage that can be treated.

Significantly, therefore, the use of meadowfoam meal as a weed inhibitor will substantially facilitate the growth of organic wheat. Certified organic crop acreage in the U.S. increased by 11 percent between 2001 and 2003, and organic wheat production, for example, increased by 30% between 2004 and 2005 (USDA Economic Research Service, 2006). Organic wheat acreage is growing in the Pacific Northwest area and neighboring states. Montana reported the largest acreage of organic wheat in 2005 of over 13,600 ha. Total 2005 organic wheat acreage in 11 western states was 36,000 ha (USDA Economic Research Service, 2006). This acreage represents a large and growing potential market for alternative cropping and weed control methods, including the use of meadowfoam meal. Downy brome is a prominent plant pest affecting wheat production in the western United States (Stougaard et al., 2004).

According to particular aspects, the inventive herbicidal and alleleopathic compositions have utility for controlling a broad variety of target weeds/plants, including grassy and broadleaf weeds (see also Machado, S., *Agronomy Journal*, 99:127-132, 2007; showing inhibition of downy brome and wheat germination by various plant root and shoot extracts including root and shoot extracts of meadowfoam (*Limnanthes alba* Hartw.). Exemplary target weeds/plants include, but are limited to Velvetleaf, Sicklepod, Milo, Pitted morning glory, Johnson grass, Barnyardgrass, downy brome (*Bromus tectorum* L.), Russian Thistle (*Salsola iberica* Sennen), Kochia (*Kochia scoparia* (L.) Schrad), Knotweed (*Polygonum aviculare* L.), lambsquarters (*Chenopodium berlandierei* Moq.), mustard (*Brassica kaber* (CD) L.C. Wheeler), Jointed goatgrass (*Aegilops cylindrica* Host), Wild oat (*Avena fatua* L.), and Cutleaf nightshade (*Solanum trifolium* Nutt.), Rice, Wheat, Corn.

Glucosinolate Breakdown Products from Other Sources.

As disclosed herein, particular aspects provide surprisingly effective methods for converting glucosinolate (glucolimnanthin) in enzyme-inactivated spent seeds (e.g., meadowfoam seed meal, MSM) into glucosinolate breakdown products (GBPs), such as alleopathic compounds (e.g., the corresponding isothiocyanate and/or nitrile) by treating MSM with relatively small or minute amounts of fresh, enzyme-active seeds. In particular aspects, the treated MSM product comprises enhanced levels of alleopathic compounds (e.g., the corresponding isothiocyanate and/or nitrile), and has substantially greater herbicidal activity than the regular, untreated MSM.

As described above, the inventive methods can be applied to other glucosinolate-containing plant materials, (e.g., oriental mustard, papaya, garden cress, horseradish, watercress, etc.,), and therefore the GBPs and GBP-containing material (e.g., augmented meals, plant materials, or extracts) derived from such applications of the inventive methods can be used as herbicides as described herein. Such herbicidal or alleopathic utility is supported by the art. For example, Dale et al., (*Weed Science* 34:325-327, 1986) discusses the decline in phytotoxicity of benzyl ITC (Papaya (*Carica papaya*), Garden Cress (*Lepidium Sativum*)) formulated as granules. Numerous weeds were tested including velvetleaf, sicklepod, milo, and pitted morning glory, with demonstrated inhibition of germination against all weed types. The relationship of germination control and timing of ITC application was also demonstrated.

In certain aspects, the inventive herbicides are used for weed control in commercial crop (e.g., wheat) production. In alternated aspects, the inventive herbicides scope (allelopathic, germination inhibitory scope) may include wheat, which can be a 'weed' in the context of another crop. Such alleopathic uses are supported by the art. For example, Vaughn et al., (*J. Chem. Ecol* 22:1939-1949, 1996) discusses the allelopathic activity of 3-methoxyphenyl acetonitrile, 3-methoxybenzyl ITC (Meadowfoam (*L. alba*)) on wheat, and demonstrated that the ITC had greater activity against wheat and velvet leaf. Likewise, Bialy, Z., et al., (*Plant and Soil,* 129:277-281, 1990) discusses alleopathic potential of glucosinolates (e.g., mustard oil glycosides) and GBPs (allyl ITC (Oriental Mustard (*Brassica Juncea*)), benzyl ITC (Papaya (*Carica papaya*), Garden Cress (*Lepidium Sativum*)), and 2-phenylethyl ITC (Horseradish (*Cochlearia Armoracia*)), Watercress (*Nasturtium officinalis*)) against wheat; order of effectiveness: 2-phenylethyl ITC>allyl ITC>benzyl ITC.

Fungicidal Utilities:

In additional aspects, the inventive compositions have substantial utility as fungicidal agents. As described above, the inventive methods can be applied to other glucosinolate-containing plant materials, (e.g., oriental mustard, papaya, garden cress, horseradish, watercress, etc.,), and therefore the GBPs and GBP-containing material (e.g., augmented meals, plant materials, or extracts) derived from such applications of the inventive methods can be used as fungicides as described herein. Such uses are supported in the art.

For example, Mari et al. (*Ann. Appl. Biol.* 123:155-164, 1993) discuss in vitro activity of glucosinolate-derived isothiocyanates (e.g., trans-4-methylthio-3-butenyl ITC A (Radish (*Raphanus sativus*), Wasabi (*Wasabia japonica*)), 3-butenyl ITC B (Rapeseed (*Brassica napus*)), 2-propenyl ITC C (Oriental Mustard (*Brassica Juncea*)), benzyl ITC (Papaya D (*Carica papaya*), Garden Cress (*Lepidium Sativum*)), and 4-hyxdroxybenzl E (Yellow Mustard (*Sinapis alba*)) against postharvest fruit pathogens. While the intact glucosinolates showed no activity against 5 common fruit pathogens, there was activity against spore germination (activity of A, C, and E above were equal, with lower activity reported for D and B). The minimum inhibitory concentrations were reported for A, C, and B, where the activity varied based on molecular species and fungal species.

Likewise, a paper published in Food Technology (P. J. Delaquis et al., Food Tech., 11: 73-84, 1995) discusses 2-phenylethyl ITC A (Horseradish (*Cochlearia Armoracia*), Watercress (*Nasturtium officinalis*)), benzyl ITC B (Papaya (*Carica papaya*), Garden Cress (*Lepidium Sativum*)), 4-methylthio-3-butenyl C (Radish (*Raphanus sativus*), Wasabi (*Wasabia japonica*)), showing that A, B, and C had good activity against fungi. The authors cite research that shows increased activity with aromatic ITCs.

Moreover, Lewis et al., show an effect of sulfur-containing volatile compounds and vapors from cabbage decomposition on *Aphamyces euteiches*. Compounds studied were methyl ITC A, allyl ITC B (Rapeseed (*Brassica napus*)), butyl ITC C, and 2-phenylethyl ITC D (Horseradish (*Cochlearia Armoracia*), Watercress (*Nasturtium officinalis*)). The compounds were tested against pathogen causing pea root rot, and compounds A and B performed well, and outperformed C and D.

Insecticidal Utilities:

In additional aspects, the inventive compositions have substantial utility as insecticidal agents. As described above, the inventive methods can be applied to other glucosinolate-containing plant materials, (e.g., oriental mustard, papaya, garden cress, horseradish, watercress, etc.,), and therefore the GBPs and GBP-containing material (e.g., augmented meals, plant materials, or extracts) derived from such applications of the inventive methods can be used as insecticides as described herein. Exemplary utilities include, but are not limited to nematocidal activity, activity against fall armyworm, activity against wireworms, etc. Such uses are supported in the art.

For example, Bartelt et al., (*J. Econ. Entol.* 82:1054-1060, 1989) discuss toxicity of compounds derived from *L. alba* seed to fall armyworm (*Lepidoptera*: Noctuidae) and European corn borer (*Lepidoptera*: Pyralidae) larvae. Compounds studied included 3-methoxybenzyl ITC A (Meadowfoam (*L. alba*)), benzyl ITC B (Papaya (*Carica papaya*), Garden Cress (*Lepidium Sativum*)), and related synthetic analogs. Compound A was more effective than B and the synthetic analogs against armyworm. The compounds were somewhat less effective against European corn borer.

Likewise, Buskov et al. (*J. Agric. Food Chem.* 50:690-695, 2002) discuss effects of intact glucosinolates and products produced from glucosinolates in myrosinase-catalyzed hydrolysis on the potato cyst Nematode (*Globodera rostochiensis* Ct. Woll). Compounds studied included prop-2-enyl ITC A (Oriental Mustard (*Brassica Juncea*)), but-3-enyl ITC B (Rapeseed (*Brassica napus*)), 4-hydroxybenzyl ITC C (Yellow Mustard (*Sinapis alba*)), 4-methylsulfinylbutyl-3-enyl ITC D (Broccoli (*Brassica Oleracia* var. *Italica*)), 2-hydroxybut-3-enyl ITC E (*Crambe* (*Crambe abysinnica*), Rapeseed (*Brassica napus*)), 2-hydroxy-2-phenylethyl ITC F, 2-phenylethyl ITC G ( ): Horseradish (*Cochlearia Armoracia*), Watercress (*Nasturtium officinalis*)), and benzyl ITC H (Papaya (*Carica papaya*), Garden Cress (*Lepidium Sativum*)). Compounds A, G, and H performed well, whereas the intact glucosinolates showed no activity.

Additionally, Potter et al., (*J. Chem. Ecol.* 24:67-80, 1997) discuss the suppressive impact of glucosinolates in *Brassica* vegetative tissues on root lesion nematode (*Pratylenchus neglectus*). The compound studied was 2-phenylethyl ITC (horseradish (*Cochlearia Armoracia*), Watercress (*Nasturtium officinalis*)). The results showed suppression of root lesion nematode.

Moreover, Brown, et al. (*J. Chem. Ecol.* 17:2021-2034, 1991) discuss allelochemicals produced during glucosinolate degradation in soil. The compound studied was allyl ITC (rapeseed (*Brassica napus*)). The result showed that rapeseed derived GBPs deterred late instar wireworms. The authors conclude that ITCs (as represented by allyl ITC) are responsible, but that activity might also derive from ionic thiocyanates.

Likewise, Williams et al. (*J. Chem. Ecol.* 19:1033-1046, 1993) discuss the toxicity of allyl ITC-amended soil to *Limonius californicus* (Mann.) (*Coleoptera*: Elateridae) wireworms. The compound studied was allyl ITC (rapeseed (*Brassica napus*)). The authors determined $LC_{50}$s for test compound against the target pest.

Pharmaceutical/Therapeutic Utilities:

In additional aspects, the inventive compositions have substantial therapeutic utility. As described above, the inventive methods can be applied to other glucosinolate-containing plant materials, (e.g., oriental mustard, papaya, garden cress, horseradish, watercress, etc.,), and therefore the GBPs and GBP-containing material (e.g., augmented meals, plant materials, or extracts) derived from such applications of the inventive methods can be used as therapeutic agents as described herein. Exemplary utilities include, but are not limited to administration, to a subject in need thereof, a therapeutically effective amount the inventive compositions for treatment and/or prevention of cancer, chemoprotectant, anti-aging, bacteriostatic, bactericidal, treatment and/or prevention of ulcers, treatment and/or prevention of gastritis, treatment of skin disorders including but not limited to eczema, facial eczema, dermatitis, external ulcers, welts, rashes, insect bites, allergic reactions and other irritations, burns, wounds, psoriasis, acneiform eruptions, dryness, dry skin, irritation, skin atrophy, secondary infections and the like. Such uses are supported in the art. "Chemoprotectants" and "chemoprotective compounds" refer to agents of plant origin that are effective for reducing the susceptibility of mammals to the toxic and neoplastic effects of carcinogens. As used herein, "therapeutically effective amount" is an amount which provides the desired effect or benefit upon administration; generally, about 1 to about 50 mg per single dosage of a pharmaceutical composition.

For example, Fahey et al., (*PNAS* 99:7610-7615, 2002) discusses sulforaphane inhibition of extracellular, intracellular, and antibiotic-resistant strains of *Helicobacter pylori*, and prevention of benzo[a]pyrene-induced stomach tumors. The compound studied was sulforaphane (4-methylsulfinylbutyl ITC) (Broccoli, Cauliflower (*Brassica oleracea Italica*)). The results showed that the test compound blocked benzo[a]pyrene-induced stomach tumors in mice dosed with test compound. The authors also demonstrated bacteriostatic and bactericidal properties against bacteria (e.g., *Helicobacter pylori*) linked to dramatically increased risk of stomach cancer, gastritis and peptic ulcer.

Additionally, Fahey et al., (PNAS 74:10367-10372, 1997) discusses induction of phase 2 detoxification enzymes (e.g., glutathione transferases, epoxide hydrolase, NAD(P)H: quinone reductase, and glucuronosyltransferases), and inhibition of 7,12-dimethylbenz(a)anthracene (DMBA)-elicited mammary tumor formation in rats using broccoli sprout extracts containing sulforaphane. Broccoli sprouts (broccoli, cauliflower (*Brassica oleracea Italica*)) are an exceptionally rich source of chemicals (e.g., sulforaphane (4-methylsulfinylbutyl ITC)) that are induces of enzymes that protect against chemical carcinogens.

Gao et al., (*PNAS* 98:15221-15226, 2001) show indirect antioxidant effects of sulforaphane (4-methylsulfinylbutyl ITC) (Broccoli, Cauliflower (*Brassica oleracea Italica*)) by showing that the compound provides powerful and prolonged protection of human retinal pigment epithelial cells, keratinocytes, and mouse leukemia cells against oxidative damage. The authors discuss phase 2 detoxification enzymes (e.g., glutathione transferases, epoxide hydrolase, NAD(P)H: quinone reductase), and discuss the connection of oxidative stress to carcinogenesis. The authors demonstrate an increase in glutathione after treatment with sulforaphane, and show that keratinocytes were protected from oxidative stress.

The review by Talalay et al., (In American Institute for Cancer Research 11th Annual Research Conference on Diet, Nutrition and Cancer 3027S-3033S, 2001) discusses the protective effects of phytochemicals (sulforaphane (4-methylsulfinylbutyl ITC) from cruciferous plants (broccoli, cauliflower (*Brassica oleracea Italica*)) against cancer (e.g., colon, prostate, bladder, breast cancer, non-Hodgkin's lymphoma) by modulating carcinogen metabolism. The authors discuss the biochemistry surrounding Phase 2 enzyme inducers, which in addition to detoxifying electrophiles, exercise versatile, long-lasting and catalytic antioxidant protection.

Talalay et al. (*PNAS* 104:17500-17505, 2007) show that topically applied sulforaphane (4-methylsulfinylbutyl ITC) (broccoli, cauliflower (*Brassica oleracea Italica*) mobilizes cellular defenses that protect skin against damage by UV radiation. The authors discusses direct mutation of DNA by UV radiation, as well as indirect damage via oxidative stress induced by UV radiation. Erythema and inflammation induced by UV radiation are additionally discussed, and were reduced in human subjects treated with sulforaphane and exposed to UV (direct absorption of the UV by sulforaphane was excluded). Up-regulation of phase 2 enzymes was shown in mouse and human skin was after treatment with sulforaphane.

Dinkova-Kostova et al. (*Cancer Epidemiol Biomarkers Prev* 2007, 16, (4) 847-851) show induction of the phase 2 response in mouse and human skin by sulforaphane (4-methylsulfinylbuthyl ITC)-containing broccoli sprout extracts (broccoli, cauliflower (*Brassica oleracea Italica*)). The authors demonstrated that phase 2 enzyme levels were increased in mouse and human skin after topical application of sulforaphane containing extracts. The data, derived in part by using skin punch biopsies, demonstrates an increase in skin antioxidants.

Dinkova-Kostova et al. (*Cancer Letters* 240:243-252, 2006) show protection against UV-light-induced skin carcinogenesis in SKH-1 high-risk mice by topical application of sulforaphane (4-methylsulfinylbuthyl ITC)-containing broccoli sprout extracts.

The authors discuss phase 2 detoxification enzymes (e.g., glutathione transferases, epoxide hydrolase, NAD(P)H: quinone reductase), in mouse and human keratinocytes, with respect to anti-aging, and prevention of oxidative stress).

Prochaska et al., ((*PNAS* 89:2394-2398, 1992)) discuss rapid detection of inducers (sulforaphane (4-methylsulfinylbuthyl ITC)) of enzymes that protect against carcinogens. This is early paper that demonstrates the ability of crucifer extracts to elevate phase II enzymes (e.g., NAD(P)H:quinone reductase). While the results show high activity for sulforaphane, the data also supports t induction of phase II enzymes by other cruciferous and *Brassica* extracts.

The present invention provides compositions for the treatment, prophylaxis, and amelioration of a disorder in a subject. Pharmaceutical compositions comprise at least one composition of the invention, along with a pharmaceutically acceptable excipient or carrier (which are well known in the art).

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, intra-tumoral, intra-synovial and rectal administration. In various embodiments, the pharmaceutical compositions or single unit dosage forms are sterile and in suitable form for administration to a subject, preferably an animal subject, more preferably a mammalian subject, and most preferably a human subject.

The composition, shape, and type of dosage forms of the invention will typically vary depending on their use. Examples of dosage forms include, but are not limited to: tablets; caplets; capsules, such as soft elastic gelatin capsules; pills, pellets, capsules containing liquids cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. Formulations in the form of powders or granulates may be prepared using the ingredients mentioned above under tablets and capsules in a conventional manner using, e.g., a mixer, a fluid bed apparatus or a spray drying equipment.

Generally, a dosage form used in the acute treatment of a disorder may contain larger amounts of one or more of the active ingredients it comprises than a dosage form used in the chronic treatment of the same disease. Also, the prophylactically and therapeutically effective dosage form may vary among different types of disorders. Similarly, a parenteral dosage form may contain smaller amounts of one or more of the active ingredients it comprises than an oral dosage form used to treat the same disease or disorder. These and other ways in which specific dosage forms encompassed by this invention will vary from one another and will be readily apparent to those skilled in the art. See, e.g., Remington's Pharmaceutical Sciences, Gennaro, et al., 19th Ed., Easton, Pa., Mack Publishing Co., (1995); Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J. C. Boylan, Marcel Dekker, Inc., New York, 1988, which are incorporated herein by reference in their entirety.

The invention also provides that a pharmaceutical composition can be packaged in a hermetically sealed container such as an ampoule or sachette indicating the quantity. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Dosage and Frequency of Administration:

The amount of the compound or composition of the invention which will be effective in conjunction with a particular method will vary e.g., with the nature and severity of the disorder and the route by which the active ingredient is administered. The frequency and dosage will also vary according to factors specific for each subject, such as age, body, weight, response, and the past medical history of the subject. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (58.sup.th ed., 2004). Exemplary doses include milligram or microgram amounts of the compound of the invention per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Cosmetic and Cosmeceutical Utilities:

In additional aspects, the inventive compositions have substantial cosmetic and/or cosmeceutical utility. As described above, the inventive methods can be applied to other glucosinolate-containing plant materials, (e.g., oriental mustard, papaya, garden cress, horseradish, watercress, etc.,), and therefore the GBPs and GBP-containing material (e.g., augmented meals, plant materials, or extracts) derived from such applications of the inventive methods can be used as cosmetic and/or cosmeceutical agents as described herein. Exemplary utilities include, but are not limited to skin creams and ointments, moisturizing creams and ointments, sun screen compositions, anti-aging compositions, anti-oxidant compositions, lotions, night creams, make-up, after sun products, and eye creams, etc. Such uses are supported in the art.

For example, Gao et al., (*PNAS* 98:15221-15226, 2001), discussed above in relation to cancer, show indirect antioxidant effects of sulforaphane (4-methylsulfinylbuthyl ITC) (Broccoli, Cauliflower (*Brassica oleracea Italica*)) by showing that the compound provides powerful and prolonged protection of human retinal pigment epithelial cells, keratinocytes, and mouse leukemia cells against oxidative damage. The authors discuss phase 2 detoxification enzymes (e.g., glutathione transferases, epoxide hydrolase, NAD(P)H: quinone reductase), and discuss the connection of oxidative stress to carcinogenesis. The authors demonstrate an increase in glutathione after treatment with sulforaphane, and show that keratinocytes were protected from oxidative stress.

Additionally, Talalay et al. (*PNAS* 104:17500-17505, 2007), discussed above in relation to cancer, show that topically applied sulforaphane (4-methylsulfinylbuthyl ITC) (broccoli, cauliflower (*Brassica oleracea Italica*) mobilizes cellular defenses that protect skin against damage by UV radiation. The authors discuss direct mutation of DNA by UV radiation, as well as indirect damage via oxidative stress induced by UV radiation. Erythema and inflammation induced by UV radiation are additionally discussed, and were reduced in human subjects treated with sulforaphane and exposed to UV (direct absorption of the UV by sulforaphane was excluded). Up-regulation of phase 2 enzymes was shown in mouse and human skin was after treatment with sulforaphane. The data also support utility for cosmetic and cosmeceutical applications, because it can reduce oxidative stress that leads to photoaging, support anti-aging claims on products, and add the functionality of reducing redness/ erythema to suncare products.

Dinkova-Kostova et al. (*Cancer Epidemiol Biomarkers Prev* 2007, 16, (4) 847-851), discussed above in relation to cancer, show induction of the phase 2 response in mouse and human skin by sulforaphane (4-methylsulfinylbuthyl ITC)-containing broccoli sprout extracts (broccoli, cauliflower (*Brassica oleracea Italica*)). The authors demonstrated that phase 2 enzyme levels were increased in mouse and human skin after topical application of sulforaphane containing extracts. The data, derived in part by using skin punch biopsies, demonstrates an increase in skin antioxidants. The data also support utility for cosmetic and cosmeceutical applications (e.g., anti-aging, etc).

Dinkova-Kostova et al. (*Cancer Letters* 240:243-252, 2006), discussed above in relation to cancer, show protection against UV-light-induced skin carcinogenesis in SKH-1 high-risk mice by topical application of sulforaphane (4-methylsulfinylbuthyl ITC)-containing broccoli sprout extracts. The authors discuss phase 2 detoxification enzymes (e.g., glutathione transferases, epoxide hydrolase, NAD(P)H: quinone reductase), in mouse and human keratinocytes, with respect to anti-aging, and prevention of oxidative stress). The data also support utility for cosmetic and cosmeceutical applications (e.g., anti-aging, etc).

In another embodiment, the present invention provides cosmetic compositions comprising one or more compositions or compounds of the invention and a cosmetic agent. The cosmetic compositions of the present invention can be utilized for providing healthful, therapeutic and aesthetic skin and/or hair benefits by contacting, deposition and/or adhesion to skin, or by providing and maintaining body hygiene.

The cosmetic compositions can be formulated in a number of ways, including but not limited to emulsions. In emulsion technology, an emulsion is a composition comprising a "dispersed phase" and a "continuous phase," with the dispersed phase existing as small particles or droplets that are suspended in and surrounded by the continuous phase. For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The cosmetic compositions of the present invention can be formulated into a wide variety of product types, including creams, waxes, pastes, lotions, milks, mousses, gels, oils, tonics, and sprays. Preferred compositions are formulated into lotions, creams, gels, and sprays. These product forms may be used for a number of applications, including, but not limited to, soaps, shampoos, hair, hand and body lotions, cold creams, facial moisturizers, anti-acne preparations, topical analgesics, make-ups/cosmetics including foundations, eyeshadows, lipsticks, and the like. Any additional components required to formulate such products vary with product type and can be routinely chosen by one skilled in the art.

If compositions of the present invention are formulated as an aerosol and applied to the skin as a spray-on product, a propellant is added to the composition. Examples of suitable propellants include chlorofluorinated lower molecular weight hydrocarbons.

The present compositions and methods, therefore, have substantial utility for many uses, including the exemplary uses described herein.

The following examples describe illustrative methods of practicing the instant invention and are not intended to limit the scope of the invention in any way.

Materials and Methods

General. NMR experiments were performed on a Bruker DPX400 instrument. High-resolution FAB-MS measurements were conducted on a JEOL JMS-600H double-focusing magnetic sector mass spectrometer.

Chemicals. HPLC water was produced from reversed-osmosis water by a Milli-Q water purification system. HPLC-grade acetonitrile and methanol were purchased from EMD Chemicals (San Diego, Calif.). 3-Methoxyphenylacetonitrile 2 ("MPAN") was purchased from Sigma Aldrich, St. Louis, Mo. 3-Methoxybenzyl isothiocyanate 3 ("MBITC") was obtained from Oakwood Products, West Columbia, S.C. 2-(3-Methoxyphenyl) acetamide (4) was from Maybridge Trevillett, Tintagel, Cornwall, U.K.

HPLC. The HPLC equipment consisted of a Waters Delta 600 solvent delivery system, a Waters 717 plus Autosampler, a Waters 2996 photodiode array detector, a Waters 600 controller and a data acquisition/processing computer with Empower™ software (Waters, Milford, Mass.). In HPLC system 1, separations were achieved on a reverse-phase Lichrosphere 5 µm C18 column (4×250 mm, Phenomenex, Torrance, Calif.). The HPLC solvents were 0.1% aqueous trifluoroacetic acid (solvent A) and MeCN (solvent B). A linear solvent gradient was employed starting from 5% solvent B in solvent A to 100% B over 30 min at a flow rate of 1.0 mL/min. After returning to the starting conditions in 1 min, the column was equilibrated for 10 min before the next injection. The injection volume was 20 µL. On-line UV spectra were recorded in the range 220-500 nm and the λ274 nm trace was used for calculation of peak areas. Analyte concentrations were determined from calibration curves constructed for each analyte.

In HPLC system 2, used for monitoring fractions from a Sephadex LH-20 column, the HPLC column was an Agilent Zorbax 5 µm SB-C18 column (2.1×50 mm). The column was eluted with solvent A for 2 min, then solvent B was increased to 100% over 5 min, held at 100% for 0.5 min and decreased to 0% solvent B (100% solvent A). The column was equilibrated at 100% solvent A for 2.4 min before the next injection. The flow rate was 0.3 mL/min and the injection volume was 1.0 μL.

Isolation of glucolimnanthin 1 ("GLN") from meadowfoam seed meal. Factory-grade meal (250 g; Natural Plant Products Inc., Salem, Oreg.) was soaked in 500 mL MeOH-water (1:1, v/v, 'extraction solvent') for 18 hrs and the slurry transferred to a 2 L percolator fitted at the bottom with a cotton plug and cotton cloth. Extraction solvent (2.4 L) was passed through the column of seed meal at a flow rate of 0.2 L/hr. Three fractions (0-0.8 L, 0.8-1.6 L and 1.6-2.4 L) were collected and analyzed by HPLC using system 1. Fractions 1 and 2 were combined and taken to dryness by rotary evaporation (careful: foaming) and lyophilization. The residue was dissolved in 50 mL of water and diluted with 300 mL of MeOH. The resulting precipitate (carbohydrates and proteins) was removed by centrifugation, and the supernatant was concentrated in vacuo. The residue was taken up in 60 mL of MeOH and four 15 mL portions were fractionated by column chromatography on Sephadex LH-20 using MeOH as the eluting solvent at a flow rate of 1.6 mL/hr. Fractions (10 mL) were collected, monitored by HPLC (system 2) for the presence of glucolimnanthin (1), and the glucolimnanthin (1)-containing fractions were combined and taken to dryness by rota-evaporation. Crude 1 obtained from two column runs (2.6 g) was redissolved in 6 mL of MeOH and purified on the same Sephadex LH-20 column using the same chromatographic conditions, yielding 1.8 g of >95% pure 1 by NMR analysis. $^1$H NMR (400 MHz, MeOH-d$_4$): $\delta_H$ 7.26 (1H, t, J=8 Hz, H-5'), 7.01 (1H, s, H-2'), 7.00 (1H, d, J=8 Hz, H-6'), 6.83 (1H, d, J=8 Hz, H-4'), 4.55 (1H, d, J=9 Hz, H-1"), 4.25 (1H, d, J=16 Hz, H-2), 4.05 (1H, d, J=16 Hz, H-2), 3.87 (1H, d, J=12 Hz, H-6"), 3.81 (3H, s, CH$_3$), 3.63 (1H, dd, J=5, 12 Hz, H-6"), 3.37-3.25 (2H, m, H-3" and H-4"), 3.21-3.12 (2H, m, H-2" and H-5"). $^{13}$C NMR (100 MHz, MeOH-d$_4$): $\delta_C$ 160.2 (C-3'), 159.5 (C-1), 137.6 (C-1'), 129.5 (C-5'), 120.2 (C-6'), 113.1 (C-2'), 112.6 (C-4'), 81.5 (C-1"), 80.9 (C-2"), 78.0 (C-3"), 72.8 (C-5"), 69.8 (C-4"), 61.4 (C-6"), 54.3 (CH$_3$), 38.3 (C-2). Assignment of these resonances was confirmed by $^1$H-$^1$H COSY, $^1$H—$^{13}$C HSQC and HMBC experiments.

Preparation of fermented meal products. Fermented meal was prepared, for example, by grinding 9.9 g meal together with 0.1 g of untreated meadowfoam seed (*Limnanthes alba* ssp. *alba* Benth., cultivar Ross) in a coffee grinder (model E160B, Proctor Silex, Washington, N.C.) for one minute. Ground batches were pooled and mixed with de-ionized water (3 ml/g meal), sonicated for five minutes, allowed to incubate for 18 hours at room temperature, freeze-dried, and re-ground for 30 seconds. Iron-augmented meal was produced by the same procedure except 10 mM FeSO$_4$ was substituted for de-ionized water. Control incubations, all without added seeds, included unaltered meal (ground but not incubated with water), sham-augmented meal (meal plus water alone), iron only (meal plus 10 mM FeSO$_4$).

For analysis of the fermented meal products, 1.0 g aliquots of the fermented meal products were mixed with 6 ml of 50% methanol in screw-capped glass centrifuge tubes, vortexed for 30 seconds, and sonicated for 60 seconds. The glass tube contents were allowed to stand overnight in the dark at room temperature, vortexed and sonicated again, and centrifuged for 5 minutes on a clinical centrifuge. Supernatants were further centrifuged for ten minutes at 13,000 rpm using a micro-centrifuge, diluted 1:9 with 50% methanol, and then analyzed directly by HPLC. Samples were prepared in triplicate.

Assay for herbicidal activity. About 45 g of clean soil was weighed into 10-cm diameter Petri dishes. For germination testing of individual compounds (1-4), 15.0 mL of test solution was added to each dish. Glucolimanthin 1 (GLN) was dissolved in water and compounds 2-4 in ethanol. The ethanolic solutions were applied to the dishes, allowed to evaporate overnight in a hood, and then 15 mL of water was added to the dishes. Meal products were mixed with soil, followed by the addition of 15 mL of water. Fifteen seeds of Bromus tectorum were placed in concentric circles within each dish. Petri dishes with lids were placed in an incubator at 20° C. during day time (8 hrs) and at 15° C. at night time (16 hrs) for 7 days. Germination was recorded as root emergence.

Example 1

GLN, MPAN and MBITC were Detected and Quantified in Meadowfoam Products (MSM) by Phytochemical Analysis Phytochemical Analysis.

Applicants initially developed analytical methods based on HPLC for the detection and quantification of the glucosinolate glucolimnanthin 1 ("GLN"), the corresponding isothiocyanate 3 ("MBITC"), and the corresponding nitrile 2 ("MPAN") in meadowfoam products (meadowfoam seed-meal; "MSM").

Methods.

Gram amounts of GLN were isolated from MSM by methanol-water extraction and purification to >95% homogeneity by repetitive chromatography on Sephadex LH-20. GLN was obtained as the potassium salt as indicated by fast-atom bombardment mass spectrometry (FAB-MS) in the positive ion mode. The presence of MPAN and MBITC in seeds and MSM, respectively, was confirmed by HPLC-UV comparison with authentic standards purchased from a commercial source.

Results.

Bulk MSM, provided by Natural Plant Products, Inc., contained up to 4% GLN, up to 0.6% MPAN, and virtually no MBITC. Meadowfoam (*Limnanthes alba*) seed material, obtained from the Department of Crop and Soil Science at OSU, was found to contain about 3% GLN after heat-treatment to inactivate myrosinase.

Analysis of particular meadowfoam seed meal by HPLC-UV shows glucolimnanthin 1 (3.6% by weight) and its degradation product 2 (0.34%) as the main constituents containing the 3-methoxybenzyl moiety (UV$_{max}$ 274 nm, FIG. 2A and Table 1). The presence of substantial amounts of nitrile 2 in the meal is attributed to heat-induced degradation of glucolimnanthin 1 during the industrial extraction process, because untreated meadowfoam seeds contain primarily 1 and only very small amounts of 2 (data not shown). This finding is consistent with continuous thermal formation of benzyl cyanide from benzylglucosinolate in seeds of the garden cress (*Lepidium sativum*) after heat-inactivation of myrosinase (8). The retention of 2 in meadowfoam seed meal after hexane extraction and 2 having sufficient solubility in hexane suggest that the thermal conversion of 1 took place after oil extraction when the meal undergoes steaming to remove residual extraction solvent. The acetamide 4 was virtually undetectable in the meal, indicating that hydrolysis of 2 during meal steaming is negligible.

Example 2

'Inoculation' of Myrosinase-Inactive MSM with Small Amounts of Ground, Myrosinase-Active Meadowfoam Seed (e.g., 1%) Resulted in Significant Conversion of GLN into MBITC Applicants conceived that the allelopathic activity of meadowfoam seedmeal (MSM) is due to glucosinolate glucolimnanthin (GLN) degradation products, and therefore investigated chemical and enzymatic ways to degrade GLN in MSM. The commercial extraction of oil from meadowfoam seeds involves a heating step in order to avoid contamination of the oil with the apolar degradation products of GLN, primarily the corresponding nitrile (MPAN) and the corresponding isothiocyanate (MBITC).

Significantly, Applicants discovered that 'inoculation' (e.g., treatment) of myrosinase-inactive MSM with small amounts of ground, myrosinase-active meadowfoam seed (1%) resulted in a significant conversion of GLN into MBITC when the inoculation mixture was brought into contact with water (compare panels A and B in FIG. 1). Specifically, peak 3 of panel B in FIG. 1 corresponds to the presence of MBITC, resulting from the 'inoculation.'

Specifically, FIGS. 1A and 1B show, according to particular exemplary embodiments, HPLC analysis of MeOH—$H_2O$ extracts of MSM pre-treated with a 3-fold amount of water by weight (FIG. 1A), and MSM inoculated with 1% myrosinase-active meadowfoam seeds and pre-treated with water (FIG. 1B). The HPLC separations were achieved on a reverse-phase Lichrosphere 5C18 column (4×250 mm; Phenomenex) using a gradient starting from 5% MeCN to 100% MeCN in 0.1% aqueous trifluoroacetic acid over 30 minutes at a flow rate of 1.0 ml/min. The UV trace was recorded at 274 nm. Both chromatograms have the same y-axis scale so that peak heights are comparable between chromatograms. Key to peaks: "1"=GLN (glucolimnanthin), "2"=MPAN (3-methoxyphenyl-acetonitrile), and "3"=MBITC (3-methoxybenzyl isothiocyanate). GLN, MPAN and MBITC have approximately the same molar extinction coefficients, thus it appears that some MBITC is lost during the enzymatic conversion, presumably due to reaction with other MSM constituents such as insoluble protein.

Example 3

Preparation of Augmented MSM from Myrosinase-Inactive MSM by Treating with Small Amounts of Ground, Myrosinase-Active Meadowfoam Seed (e.g., 1%)

Figure 2:
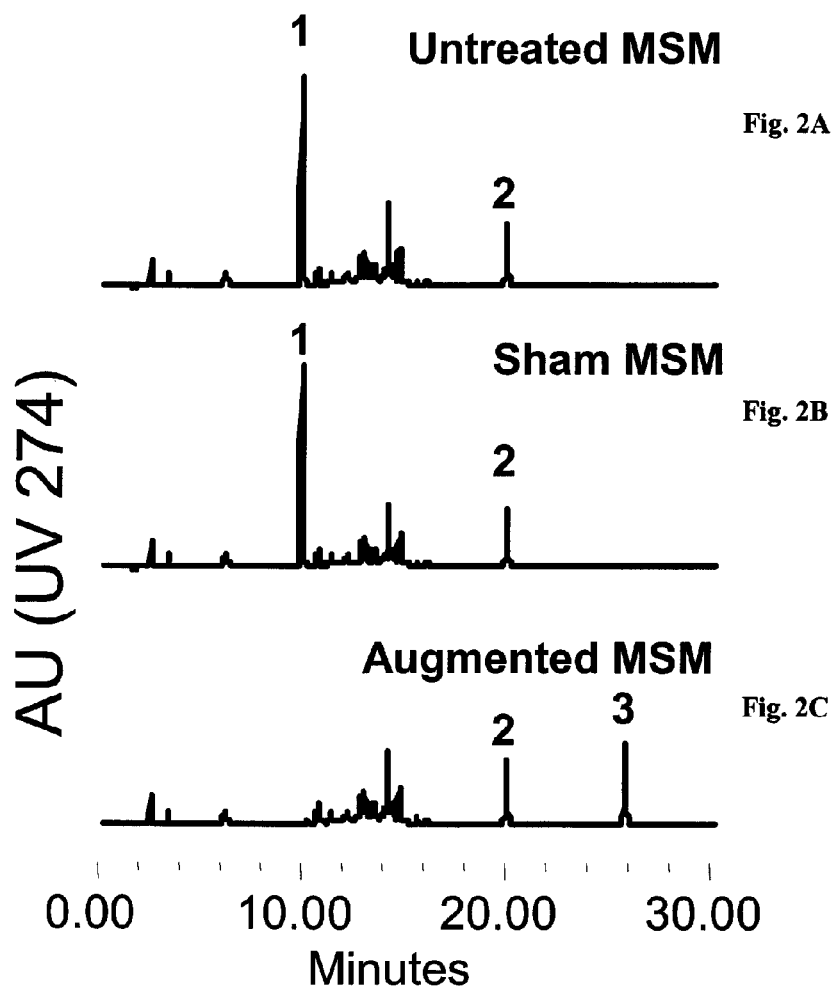
FIGS. 2A, 2B and 2C show, according to particular exemplary embodiments, HPLC analysis of untreated MSM (FIG. 2A), MSM treated with water alone (sham-treated MSM) (FIG. 2B), and MSM treated with 1% myrosinase-active meadowfoam seeds (augmented MSM) in the presence of water (FIG. 2C). The HPLC conditions and peak numbering are the same as in FIGS. 1A and 1B.

Applicants, as an initial matter, determined that glucosinolate glucolimnanthin (GLN) isolated from meadowfoam seedmeal MSM has no germination inhibitory activity when administered in an amount corresponding to the GLN level normally found in MSM. Applicants prepared MSM batches treated with 1% myrosinase-active meadowfoam seeds as described above; that is, the MSM was inoculated with ground, myrosinase-active meadowfoam seed (1%) and pre-treated with water. The treated MSM is referred to herein as "augmented MSM." Applicants reasoned that conversion of herbicide-inactive GLN into the moderately active isothiocyanate (MBITC) (3-methoxybenzyl isothiocyanate) might result in a MSM product with greater germination inhibitory activity. Because the enzymatic conversion requires addition of water that is subsequently removed, another MSM batch was treated with water but without addition of myrosinase-active seed material, to provide for "sham MSM." The augmented, sham, and untreated MSM products were analyzed by HPLC to determine the composition of the two MSM products and untreated MSM (FIG. 2).

Specifically, FIGS. 2A, 2B and 2C show, according to particular exemplary embodiments, HPLC analysis of untreated MSM (FIG. 2A), MSM treated with water alone (sham-treated MSM) (FIG. 2B), and MSM treated with 1% myrosinase-active meadowfoam seeds (augmented MSM) in the presence of water (FIG. 2C). Incubations were carried out overnight. HPLC conditions and peak numbering are the same as in FIGS. 1A and 1B.

With respect to the results of FIGS. 2A, 2B and 2C, and with respect to the germination inhibition results of FIG. 9, augmented MSM showed increased potency as a germination inhibitor as compared to untreated MSM and sham-treated MSM. The results of the germination experiments (FIGS. 8 and 9) are thus consistent with the formation of a substantial amount of MBITC from GLN, as shown in FIG. 2C.

Example 4

Directed Enzymatic Conversion of Meadowfoam-Derived GLN to MPAN was Affected Using a Broccoli Juice Preparation in the Presence of Exogenously Added $Fe^{2+}$ Species of the Brassicaceae contain nitrile-forming proteins in addition to myrosinasesm, and these nitrile-forming proteins are thought to be true enzymes rather than cofactors of myrosinases. Moreover, it has been demonstrated that $Fe^{2+}$ promotes nitrile formation in species of Brassicaceae.

In additional aspects, Applicants conceived that the herbicidal activity of MSM products might be increased by preferentially directing enzymatic conversion of GLN to the corresponding nitrile (MPAN). In this regard, Applicants incubated GLN (1 mM) with juice prepared from broccoli sprouts ('broccoli juice'), and discovered that GLN is converted into the corresponding isothiocyanate (MBITC), indicating that heterologous broccoli myrosinase accepts meadowfoam GLN as a substrate (compare panels A and C in FIG. 3).

Interestingly, when the experiment was repeated in the presence of $Fe^{1+}$ (e.g., 10 mM ferrous sulphate), GLN was mainly converted into MPAN while very little MBITC was formed (FIG. 3D), indicating that the addition of $Fe^{2+}$ activated a nitrile-forming protein (e.g., enzyme) that also accepts the heterologous GLN as a substrate. Very little conversion of GLN was observed in the presence of 10 mM $Fe^{2+}$ alone (FIG. 3B), further confirming the presence of a nitrile-forming protein (e.g., enzyme) in broccoli juice.

Specifically, FIGS. 3A, 3B, 3C and 3D show, according to particular exemplary embodiments, HPLC analysis of: GLN (1 mM, FIG. 3a); 1 mM GLN in the presence of 10 mM $Fe^{2+}$ (FIG. 3B); 1 mM GLN incubated with broccoli juice without addition of $Fe^{2+}$ (FIG. 3C); and 1 mM GLN incubated with broccoli juice in the presence of 10 mM $Fe^{2+}$ (FIG. 3D). The HPLC conditions and peak numbering are the same as in FIGS. 1A and 1B, discussed above under EXAMPLE 2.

This experiment demonstrates, according to particular embodiments, that enzymatic conversion of GLN can be directed to MPAN.

Example 5

Demonstration that Meadowfoam Seeds Contain a Nitrile-Forming Enzyme that can be Exploited to Produce an MSM Product with Enhanced Levels of MPAN The results shown in working EXAMPLE 4 above raised the question as to whether meadowfoam seeds contain a nitrile-forming enzyme that could be exploited to produce an MSM product with enhanced levels of MPAN. FIG. 1, discussed under working EXAMPLE 2 above, shows that untreated MSM contains MPAN (about 0.4%), which is likely formed during heat-treatment of seeds as part of the oil extraction process.

Figure 4:
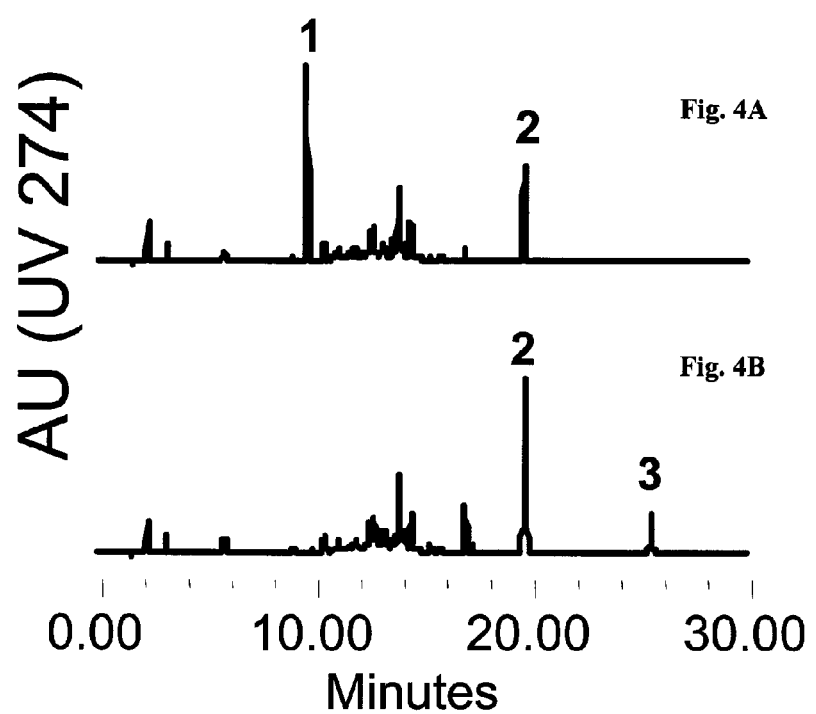
FIGS. 4A and 4B show, according to particular exemplary embodiments, HPLC analysis of MSM incubated with a 10 mM solution of $FeSO_4$ in the absence (FIG. 4A), and the presence (FIG. 4B) of 1% myrosinase-active meadowfoam seeds.

Incubation of MSM with a solution of $FeSO_4$ (10 mM) had no significant effect on the composition and very little extra MPAN was formed (FIG. 4, panel A). However, when MSM was 'inoculated' with myrosinase-active meadowfoam seeds and the mixture incubated with a 10 mM solution of $FeSO_4$, a substantial amount of MPAN was formed (e.g., compare panels A and B in FIG. 4), indicating that meadowfoam seeds contain an $Fe^{2+}$-dependent nitrile-forming enzyme in addition to myrosinase.

Specifically, FIGS. 4A and 4B show, according to particular exemplary embodiments, HPLC analysis of MSM incubated with a 10 mM solution of $FeSO_4$ in the absence (FIG. 4A), and the presence (FIG. 4B) of 1% myrosinase-active meadowfoam seeds. The HPLC conditions and peak numbering are the same as in FIGS. 1A and 1B.

Likewise FIGS. 10A, 10B and 10C show HPLC analysis of untreated meal (panel A), meal treated with 1% myrosinase-active meadowfoam seeds (panel B), and meal incubated with a 10 mM solution of $FeSO_4$ in the presence of 1% myrosinase-active meadowfoam seeds (panel C). The UV trace was recorded at 274 nm.

Table 1 shows the Composition of treated and untreated meadowfoam seed meal.

TABLE 1

Composition of treated and untreated meadowfoam seed meal

| | Average mg/g meal ± SD (n = 3) | | |
| --- | --- | --- | --- |
| | Glucosinolate 1 | Nitrile 2 | Isothiocyanate 3 |
| Meal + 1% seed | 0 | 3.25 ± 0.04 | 3.39 ± 0.02 |
| Meal + 1% seed + $FeSO_4$ | 0 | 7.28 ± 0.11 | 1.64 ± 0.03 |
| Meal + $FeSO_4$ | 26.66 ± 0.06 | 3.81 ± 0.01 | 0.12 ± 0.00 |
| Meal + water only | 34.29 ± 0.15 | 2.69 ± 0.04 | 0.03 ± 0.00 |
| Untreated meal | 35.93 ± 0.39 | 3.42 ± 0.05 | 0 |

According to additional aspects, therefore, an MSM product with enhanced levels of MPAN can be produced by treating MSM with myrosinase-active meadowfoam seed material in the presence of $Fe^{2+}$ (e.g., 10 mM ferrous sulphate).

Example 6

Demonstration that Heating an Aqueous Solution of Meadowfoam-Derived GLN in the Presence of $Fe^{2+}$ Causes Formation of MPAN in about 90% Yield In further aspects of the present invention, Applicants investigated the effect of heating on the degradation of GLN in the absence and presence of $Fe^{2+}$ ions.

The results of FIG. 5 show that heating (e.g., 60 minutes at 90° C.) of an aqueous solution of GLN containing 10 mM $FeSO_4$ causes formation of MPAN in about 90% yield, whereas incubation of 1 mM GLN with 10 mM $FeSO_4$ at room temperature did not result in significant degradation of GLN (see FIG. 3B).

Therefore, additional aspects of the present invention provide methods for producing MSM products with enhanced levels of MPAN comprising heating in the presence of $Fe^{2+}$ (e.g., 10 mM ferrous sulphate).

Example 7

Seed Germination Assays; MPAN and its Acetamide Analog, 2-(3-methoxyphenyl)acetamide, were Found to be More Active as Seed Germination Inhibitors than MBITC Applicants initially showed that meadowfoam seedmeal (MSM) completely inhibited the germination of downy brome (*Bromus tectorum*) when applied at a rate of about 20 mg MSM per g soil (FIG. 6) indicating that MSM is a potential herbicide for downy brome control. Moreover, additional experiments indicated that GLN had no effect on downy brome seed germination at levels corresponding to those found in the MSM experiments (2% GLN in MSM is equivalent to 0.4 mg GLN per g soil; FIG. 7).

Figure 6:
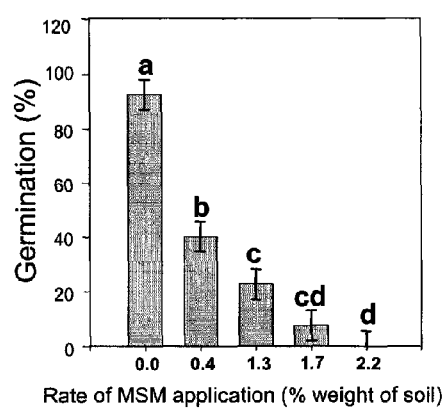
FIG. 6 shows, according to particular exemplary embodiments, the effect of MSM on downy brome seed germination. Bars with different letters indicate a significant difference ($P<0.05$, n=3).
Figure 7:
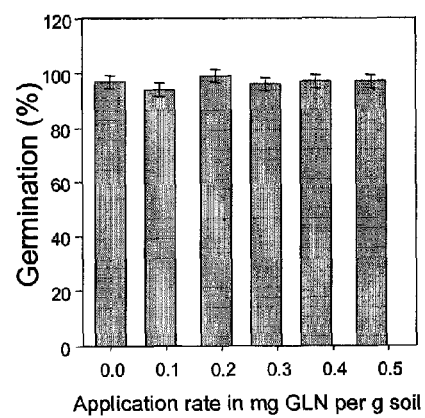
FIG. 7 shows, according to particular exemplary embodiments, the effect of glucolimnanthin on downy brome germination after 7 days of assay. No difference was observed between application rates at $P=0.5$ (n=3).

Specifically, FIG. 6 shows the effect of MSM on downy brome seed germination. Bars with different letters indicate a significant difference (P<0.05, n=3). The data indicate that the percent germination decreases with increasing amounts (% weight of soil) of applied MSN.

Specifically, FIG. 7 shows the effect of glucolimnanthin (GLN) on downy brome germination after 7 days of assay. No difference was observed between application rates at P=0.5 (n=3).

These results indicated that GLN is not the active principle component of MSM with respect to herbicidal (anti-germination) activity.

Therefore, Applicants investigated the effects of the GLN degradation products on downy brome seed germination (FIG. 8). Despite literature reports claiming that glucosinolate-derived isothiocyanates have allelopathic activity, we found that MPAN and its acetamide analog, 2-(3-methoxyphenyl)acetamide, were more active as seed germination inhibitors than MBITC (FIG. 8).

Specifically, FIGS. 8A and 8B show, according to particular exemplary embodiments, the effect of glucolimnanthin (GLN) degradation products (MPAN, Acetamide and MBITC) on downy brome germination after 82 hours (FIG. 8A) and 168 hours (FIG. 8B) of assay. The rates of application are given in mg test compound per gram soil. MPAN and its acetamide analog, 2-(3-methoxyphenyl)acetamide, were more active as seed germination inhibitors than MBITC.

Figure 11:
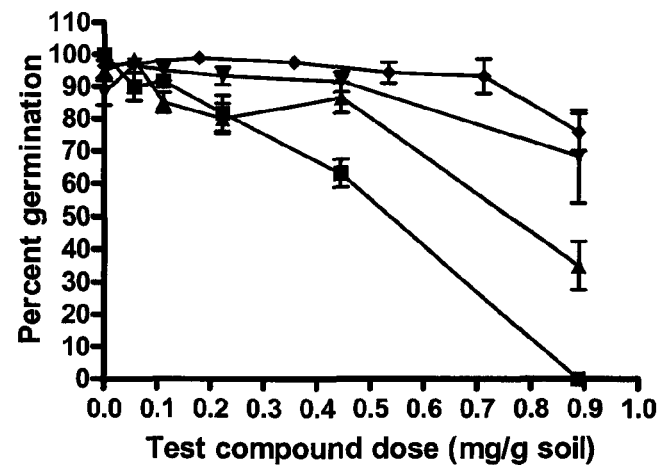
FIG. 11 shows the inhibitory effects of glucolimnanthin 1 (♦), nitrile 2 (■), isothiocyanate 3 (▼), and acetamide 4 (▲) on the germination of downy brome (Bromus tectorum) seeds. Data represent mean±SEM (n=4).

Additional assays for herbicidal activity of glucolimnanthin and degradation products showed that all glucolimnanthin degradation products tested inhibited downy brome germination (FIG. 11). FIG. 11 shows the inhibitory effects of glucolimnanthin 1 (♦), nitrile 2 (■), isothiocyanate 3 (▼), and acetamide 4 (▲) on the germination of downy brome (*Bromus tectorum*) seeds. Data represent mean±SEM (n=4). Nitrile was the most effective, completely inhibiting downy brome germination at the highest concentration tested (0.89 mg $g^{-1}$). Acetamide and isothiocyanate were not as effective and failed to completely inhibit downy brome germination even at the highest concentration. Glucolimnanthin was the least effective and only slightly inhibited downy brome germination at the highest concentration. The low efficacy of glucolimnanthin in toxicity experiments was also reported by Vaughn et al. (1996).

Applicants also investigated the effect of GLN degradation in MSM on downy brome seed germination. To achieve myrosinase-induced breakdown of GLN into MBITC, MSM was inoculated with 1% ground, myrosinase-active meadowfoam seeds and fermentation was initiated by wetting the mixture. In an initial laboratory-scale experiment, water was removed by lyophilization and the fermented MSM, termed 'augmented MSM,' was examined by HPLC (FIG. 2). The control experiment consisted of wetting MSM without addition of myrosinase-active meadowfoam seeds, termed 'sham MSM.' As shown in FIG. 9, augmented MSM showed greater inhibitory effects on seed germination than sham-treated MSM or untreated MSM (sham MSM and augmented MSM were prepared from the same MSM batch). It is also interesting to note that the untreated MSM in this experiment was not as effective as the MSM in the experiment of FIG. 6, likely due to batch-to-batch differences in levels of GLN degradation products.

Specifically, FIGS. 9A and 9B show, according to particular exemplary embodiments, the effect of MSM augmented with enzyme-active meadowfoam seed "Augm. MSM", "sham MSM" and "untreated MSM" on downy brome germination after 82 hours (FIG. 9A) and 168 hours (FIG. 9B) of assay. The rates of application are in mg MSM per gram soil. Augmented MSM showed greater inhibitory effects on seed germination than sham-treated MSM or untreated MSM.

Figure 12:
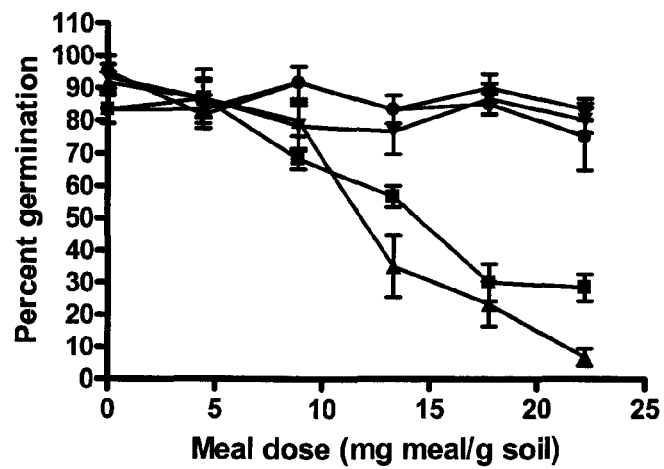
FIG. 12 shows the inhibition of germination of downy brome (Bromus tectorum) seeds by untreated meal (●) and meal incubated with ground seeds (■), with ground seeds and 10 mM $FeSO_4$ (▲), with 10 mM $FeSO_4$ (▼), or with water (♦). Data represent mean±SEM (n=4).

In additional assays of the herbicidal activity of glucolimnanthin meal products, the meals incubated with ground seeds alone and with ground seeds and iron clearly inhibited the germination of downy brome, while the untreated meal, meal treated with iron or water had no effect (FIG. 12). FIG. 12 shows the inhibition of germination of downy brome (*Bromus tectorum*) seeds by untreated meal (●) and meal incubated with ground seeds (■), with ground seeds and 10 mM $FeSO_4$ (▲), with 10 mM $FeSO_4$ (▼), or with water (♦). Data represent mean±SEM (n=4). The effectiveness of these meal preparations is enhanced by the inclusion of ground seed, which contain myrosinase, an enzyme that is responsible for hydrolyzing glucolimnanthin into its degradation products that our results showed to be herbicidal to downy brome. The meal with ground seed and iron was the most inhibitory to downy brome.

Wheat germination was also reduced by about 96% by MSM, indicating that augmented MSM will be even more efficacious for this use.

Example 8

The Inventive Methods are Broadly Applicable to Glucosinolate-Containing Plant Materials Applicants' technology represents a novel way to convert glucosinolates in spent meal (e.g., MSM), where glucosinolates are present in a wide variety of plant. Over 500 plant species contain glucosinolates, of which 16 glucosinolate families are known. According to additional aspects, the inventive methods are broadly applicable to 'glucosinolate-containing plant materials.' Exemplary glucosinolate-containing plant materials useful in practicing the present invention include, but are not limited to Brassicacae (Cruciferae), Moringaceae and Resedaceae, which collectively include, but are not limited to, broccoli, broccoli sprouts, Brussels sprouts, cabbage, cauliflower, cauliflower sprouts, daikon, horseradish, kale, mustard seed, radish, wasabi, horseradish tree (*Moringa oleifera*), cabbage tree (*M. stenopetala*), mignonette (*Reseda odorata*), dyer's rocket (*R. luteola*). Other families of plants that contain glucosinolates include, but are not limited to, Bataceae, Bretschneideraceae, Capparaceae, Caricaceae, Euphorbiaceae, Gyrostemonaceae, Limnanthaceae, Pentadiplandraceae, Phytolaccaceae, Pittosporaceae, Salvadoraceae, Tovariaceae and Tropaeolaceae (and these include plants such as capers (*Capparis spinosa*), and nasturtium (*Tropaeolum majus*)). The high levels of glucosinolates may occur naturally in plants or plants may be bred to contain higher levels or glucosinolates.

As will be appreciated by those of skill in the art, using routine methods in view of the present teachings, numerous other glucosinolate-containing plant material feedstocks, including different sources, and numerous other sources of glucosinolate-converting acitivity could be used for practicing aspects of the present invention.

In certain exemplary preferred aspects, the glucosinolate-containing plant materials comprises material from genus *Brassicas*. In particular aspects, the glucosinolate-containing plant materials (and the glucosinolate content) comprises material from at least one of the material group consisting of: Crambe (*Crambe abysinnica*, e.g., 2-hydroxybut-3-enyl ITC); Black Mustard; Yellow Mustard (*Sinapis alba*, e.g., p-hydroxybenzyl glucosinolate; Oriental Mustard (*Brassica juncea*, 2-propenyl glucosinolate (aka sinigrin, which degrades to allyl ITC); Broccoli (*Brassica oleracea italica*, sulforaphane (4-methylsufinylbutyl ITC), glucoraphanin (parent glucosinolate)); Rapeseed (*Brassica napus*, 3-butenyl ITC); Meadowfoam (*Limnanthes alba*), Radish (*Raphanus sativus*, 4-methylthio-3-butenyl ITC); Wasabi (*Wasabia japonica*, 4-methylthio-3-butenyl ITC); Horseradish (*Cochlearia Armoracia*, 2-phenylethyl ITC); Cauliflower (sulforaphane (4-methylsufinylbutyl ITC), glucoraphanin (parent glucosinolate)); Garden cress (*Lepidium sativum*, benzyl ITC); Watercress (*Nasturtium officinalis*, 2-phenylethyl ITC); and Papaya (*Carica papaya*, benzyl ITC).

Many myrosinase sequences are known in the art, and many myrosinase proteins have been sequenced and many coding sequences have been cloned and sequenced. For example, Table 2 lists some exemplary glucosinolate-converting enzyme activity sources, along with respective exemplary myrosinase nucleic acid and protein sequences. These sources are exemplary sources of myrosinase enzymes, nitrile-forming enzymes (e.g., epithiospecifier protein (ESP), and/or nitrile-specifier protein (NSP), etc.), myrosinase binding proteins and myrosinase-associated proteins, etc. The list is provided as being illustrative of sources of glucosinolate-converting enzyme activities for practicing aspects of the instant invention and are not intended to limit the scope of the invention in any way with respect to the sources of applicable enzyme activity (e.g., myrosinase, nitrile-forming enzymes, ESPs, NSPs, etc.) which are many, and can be of plant (seed and non-seed origin) or other origins (e.g., myrosinases are known to occur in fungi and insects, as well as other sources). Exemplary preferred myrosinases, are those myrosinase sequences, including the exemplary sequences shown in Table 2 below, which are members of an art-recognized glycosyl hydrolase superfamily (e.g., pfam00232, Glyco_hydro_1, Glycosyl hydrolase family 1). Members of this superfamily comprise highly conserved domains as appreciated in the art.

TABLE 2

Exemplary glucosinolate-converting enzyme activity sources, along with respective myrosinase exemplary nucleic acid and protein sequences.

| Myrosinase Source | | Nucleic acid sequence (accession number) (SEQ ID NO) | Protein sequence (accession number) (SEQ ID NO) |
|---|---|---|---|
| Rapeseed | Brassica napus | X60214; X79080 (SEQ ID NO: 1) (SEQ ID NO: 23) | CAA42775; CAA55685 (SEQ ID NO: 2) (SEQ ID NO: 24) |
| Horseradish | Armoracia rusticana | AY822710 (SEQ ID NO: 3) | AAV71147 (SEQ ID NO: 4) |
| Yellow Mustard | Sinapis alba | X59879 (SEQ ID NO: 5) | CAA42534 (SEQ ID NO: 6) |
| Oriental Mustard | Brassica juncea | AY014960 (SEQ ID NO: 7) | AAG54074 (SEQ ID NO: 8) |
| Broccoli | Brassica oleracea | EU004075; DQ767973 (SEQ ID NO: 9) (SEQ ID NO: 21) | ABS30827; ABG77972 (SEQ ID NO: 10) (SEQ ID NO: 22) |
| Radish | Raphanus sativus | AB042187; AB042186 (SEQ ID NO: 11) (SEQ ID NO: 13) | BAB17227; BAB17226 (SEQ ID NO: 12) (SEQ ID NO: 14) |
| Wasabi | Wasabia japonica | AB194903 (SEQ ID NO: 15) | BAE16356 (SEQ ID NO: 16) |
| Garden cress | Lepidium sativum | DQ417116 (SEQ ID NO: 17) | ABD73013 (SEQ ID NO: 18) |
| Papaya | Carica papaya | Partial sequence EU642644 (SEQ ID NO: 19) | Partial sequence ACC95418 (SEQ ID NO: 20) |
| | Brassica rapa (var. parachinensis) | AY957577 (SEQ ID NO: 25) | AAX68547 (SEQ ID NO: 26) |
| Thale cress | Arabidopsis thaliana putative myrosinase TGG2 | AF360348; AY054237 (SEQ ID NO: 27) (SEQ ID NO: 29) | AAK28645; AAL06896 (SEQ ID NO: 28) (SEQ ID NO: 30) |

Myrosinases are β-thioglucosidases responsible for the degradation of glucosinolates (e.g., glucose residue linked by a thioglucoside bond to an amino acid derivative). Myrosinase participates in the degradation of glucosinolates to glucose, sulfate and any of the products: thiocyanates, isothiocyanates, nitriles, epithionitriles or oxazolidine-2-thiones. Certain myrosinases are present in complexes together with other proteins such as myrosinase-binding proteins (MBP) and/or myrosinase-associated proteins. All plant myrosinases characterized to date are glycosylated and are probably transported via the secretory pathway to the myrosin grains present in idioblasts called myrosin cells. In seeds of oilseed rape, for example, the myrosin cells are scattered throughout the tissue and constitute 2% to 5% of the total number of embryonic cells. Myrosinase from horseradish (Armoracia rusticana) roots has been purified and has a native molecular mass of about 130 kDa (comprising two 65 kDa subunits). The horseradish myrosinase enzyme is highly stable, has a high activity over a broad pH (e.g., pH 5.0-8.0) and temperature range (e.g., 37-45° C.).

Myrosinases are known to be active on glycosinoates from heterologous sources, likely reflecting the common glycosinolate substrate core structure.

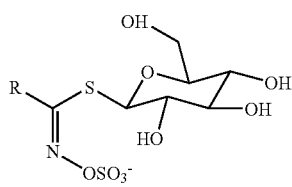

For example, like the exemplary results shown by the present Applicants herein (showing good activity of broccoli myrosinase on meadowfoam glucosinolate), the horseradish myrosinase is known to be highly active on heterologous glycosinolates. For example, while the exemplary horseradish (AAV71147) and broccoli myrosinases (ABS30827 or ABG77972) of Table 2 above share only 64% sequence identity, the horseradish enzyme has been shown (Li & Kushad, *Plant Physiol Biochem* 43:503-11, 2005) to have good activity in the breakdown of intact glucosinolates in crude extracts of broccoli. Horseradish myrosinase is known to be activated by 0.5 mM ascorbic acid (Id), and according to additional aspects of the present invention has utility as a cofactor or agent to facilitate glycosinolate breakdown in practicing certain aspects of the present invention.

Example 9

Exemplary Extraction Techniques for Preparing Oil-Depleted Seedmeal, 'Fermenting' the Oil-Depleted Seedmeal, and for Removing Glucosinolate Breakdown Products from the Fermented Seedmeals in More Concentrated Forms Applicants' disclosed technology provides novel ways to convert glucosinolate (GS) glucosinolate-containing plant materials to their more biologically active glucosinolate breakdown products (GBPs) such as isothiocyanates and nitriles.

GBPs are highly desired compounds in a number of industries including: pharmacy, veterinary, cosmetics, and agriculture.

Additionally aspects of the present invention, therefore, provide extraction technique that allow for extraction of the GBPs from the treated glucosinolate-containing plant materials, and concentration of the GBPs in a liquid form. A liquid format offers many additional formulation options, compared to those of solid, powder forms of treated glucosinolate-containing plant materials (e.g., treated MSM).

Exemplary Process Descriptions:

As described herein in particular exemplary methods, 'fermented' meal (e.g., MSM) is manufactured by combining meal with ground seed (unheated), moistening (e.g., with water or a solution of iron sulfate), holding, and freeze drying.

In additional aspects, the following techniques are employed to link the fermentation procedure to an extraction procedure to generate a liquid extract containing GBPs. The process steps described below are optimally inserted after the freeze drying step:

1. REGRINDING: According to particular aspects, regrinding the freeze dried material ensures uniformity and exposes the maximum amount of surface area, thus providing for superior extraction. As will be appreciated by one of skill in the relevant art, a variety of equipment in the oil seed and milling industry could be used for this task, including but not limited to hammer mills, disc mills, flaking rolls, cracking rolls, etc.

2. EXTRACTION: After 'regrinding,' the fermented is transferred into an extractor for solvent extraction of one or more glucosinolate breakdown products (GBPs). As will be appreciated by one of skill in the relevant art, a variety of commercially viable systems are available for this purpose, including continuous operation extractor, and batch operation extractors. Any of these may be applied to the extraction in question with varying degrees of success.

Batch extraction systems are generally composed of a sealed vessel with a perforated screen at the bottom and solvent spray head at the top. The material to be extracted is inserted into the vessel and rests above the screen. Solvent is then added to the system and flows down through the material. Typically, solvent is recirculated for a prescribed amount of time. The solvent/solvate combination is then separated and desolventized leaving the extract.

Continuous extraction systems are the standard in the vegetable oil industry. The two major manufacturers are Crown Iron Works and DeSmet. While the engineering designs are significantly different, the basic principle is the same. Briefly, the material to be extracted is placed into a vessel and flows through the unit while being rinsed with solvent. Some units are composed of distinct extraction stages where pure solvent is added during the final stage and then moves through to the first stage. Thus in the first stage, the material is extracted with solvent already containing extract. The process, known as a counter-current system, maximizes solvent performance.

Particular continuous extraction systems are designed to handle high loads of "fines." Fermented and reground meal is a representative example of fines. Fines are typically small and granular, and are different than the physical form preferred for oil extraction from seeds. Typically, seed is converted to a flaked form, or an extruded collette (much like a Cheeto), prior to extraction. These forms have good solvent drainage and have less of a tendency to clog pumps and piping than do fines.

Another extraction system comprises a centrifuge. These systems are designed to continuously extract a solid material, and then separate it from the solvent using physical forces. An inverting basket centrifuge is one commercial example of such a system.

In particularly preferred aspects of the present invention, a Crown Model IV extractor (designed to extract fines) provides an effective route of extraction.

Extraction Solvents.

According to further aspects, a variety of solvents may be used, with the particular choice of extraction solvent affecting the efficiency or degree of success. Exemplary solvents include but are not limited to alcohols, ethanol, methanol, acetone, hexane, heptane, aliphatic solvents, ethers, chlorinated solvents, chloroform, trichloroethylene, carbon dioxide, and combinations thereof. In particular aspects, preferred solvents include hexane and ethanol, and either or both may be used in practice of the disclosed methods. Additional preferred examples include the use of methanol, which is less expensive than ethanol, and the use of acetone. In particularly preferred aspects, acetone is used, because it extracts a lower content of phospholipids (PLs), which are components of seed meals that may precipitate from the resulting extract.

3. SOLVENT REMOVAL: According to additional aspects, the solvent is removed after extraction. The extracted meal and solvent bearing the extract is first segregated regardless of the type of extractor used. Meal is typically desolventized using a DT/DC (desolventizer toaster, dryer cooker). Alternatively, solvent can be removed from the extract using techniques well known in the industry. The most common system comprises a rising film evaporator, donut distillation column, and mineral oil system.

Exemplary Extraction Techniques for Preparing Oil-Depleted Seedmeal, 'Fermenting' the Oil-Depleted Seedmeal, and for Removing Glucosinolate Breakdown Products from the Fermented Seedmeals in More Concentrated Forms:

Preparation of Oil-Depleted Seedmeal.

Figure 13:
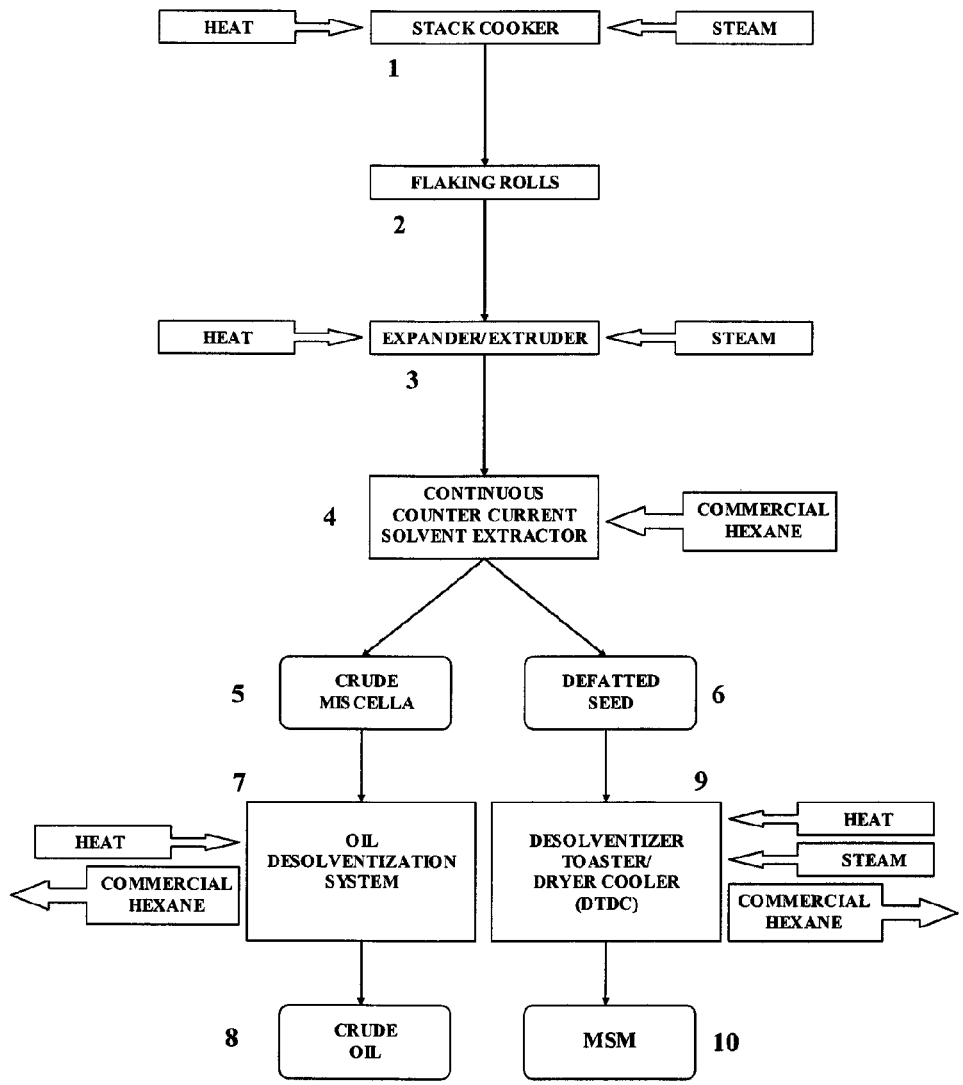
FIG. 13 shows, according to particular exemplary aspects, an exemplary commercial meadowfoam seed extraction process (e.g., to produce meadowfoam seedmeal (MSM).

FIG. 13 shows, according to particular exemplary aspects, an exemplary commercial meadowfoam seed extraction process (e.g., to produce meadowfoam seedmeal (MSM)).

With reference to FIG. 13, meadowfoam seed is loaded into the top of a continuous stack cooker 1 consisting of five cylindrical cooking chambers. Seed is agitated in each chamber by a sweeping arm and moves in a downward manner through the unit via a series of gates and chutes. The unit provides for indirect heating of seed via steam jacketing in the chambers, as well as direct heating and moisture addition via steam injection. In addition, the unit can be used to remove moisture from the seed. The unit is operated in such a fashion that core seed temperature reaches about 91° C. (e.g., 195° F.) for at least 20 minutes. This ensures deactivation of myrosinase prior to seed structure violation whereupon glucosinolates and enzyme would come into contact.

After exiting the stack cooker 1, cooked, enzyme-deactivated seed is conveyed to a set of flaking rolls 2 consisting of opposed steel rolls rotating in opposite directions at a high velocity. Seed cascades through the rolls 2 and is crushed to a thickness of approximately 0.3 mm to ensure rupture of oil cells.

Cooked, crushed, enzyme-deactivated seed is then conveyed to an expander 3 for conversion to 'extraction cake' ('extruded seed cake'). Briefly, in the expander 3, flaked seed is placed under high pressure by means of a process screw driving the flakes along a conical barrel which gradually reduces in diameter. Process pressure is controlled by means of a hydraulically operated choke at the end of the barrel. Heat is optionally added along the barrel length. Prior to exiting via the choke, live steam is injected. The mixture of seed and high pressure steam exits the unit and rapidly expands to form a porous, 'extruded seed cake.' The final process temperature is typically around 116° C. (e.g., 240° F.).

Expander cake ('extruded seed cake') is conveyed via a vibrating conveyor to a continuous countercurrent extractor 4 (e.g., manufactured by Crown Iron Works, Minneapolis, Minn.). Seed moves through stages of the extractor 4 on screens in a shallow bed arrangement. Hexane is washed over the cake in such a fashion that fresh hexane is added at the final extraction stage and is pumped backwards through the earlier stages so that newly added cake is washed with a solvent already laden with oil. After the last extraction stage, crude miscella 5, a mixture of crude oil and hexane, is pumped from the extractor, and the defatted seed cake 6, still laden with hexane, is conveyed out of the extraction unit 4.

Crude miscella 5 is pumped to the solvent distillation system 7. Here, hexane is recovered for storage and eventual reuse, and crude oil 8 is generated for storage or immediate refining. Solvent laden, defatted seed cake 6 is transferred via conveyor to a desolventizer toaster/dryer cooler (DTDC) 9 (e.g., from Crown Iron Works, Minneapolis, Minn.). This unit 9 is similar in design to the stack cooker 1 described earlier in that it consists of a series of cylindrical chambers connected by vertical chutes. However, the DTDC 9 differs from the stack cooker 1 in that it is designed to strip and recover the hexane remaining in the meal. Both indirect heat (jacketing) and direct heat via steam is added to the seed cake and hexane is driven from the matrix creating meadowfoam seedmeal (MSM) 10. The skilled application of heat will also result in a moisture level of about 10-12%, which is optimal for storage of MSM 10.

'Fermenting' the Oil-Depleted Seedmeal, and Removing Glucosinolate Breakdown Products (GBPs) Therefrom in Concentrated Forms.

Figure 14:
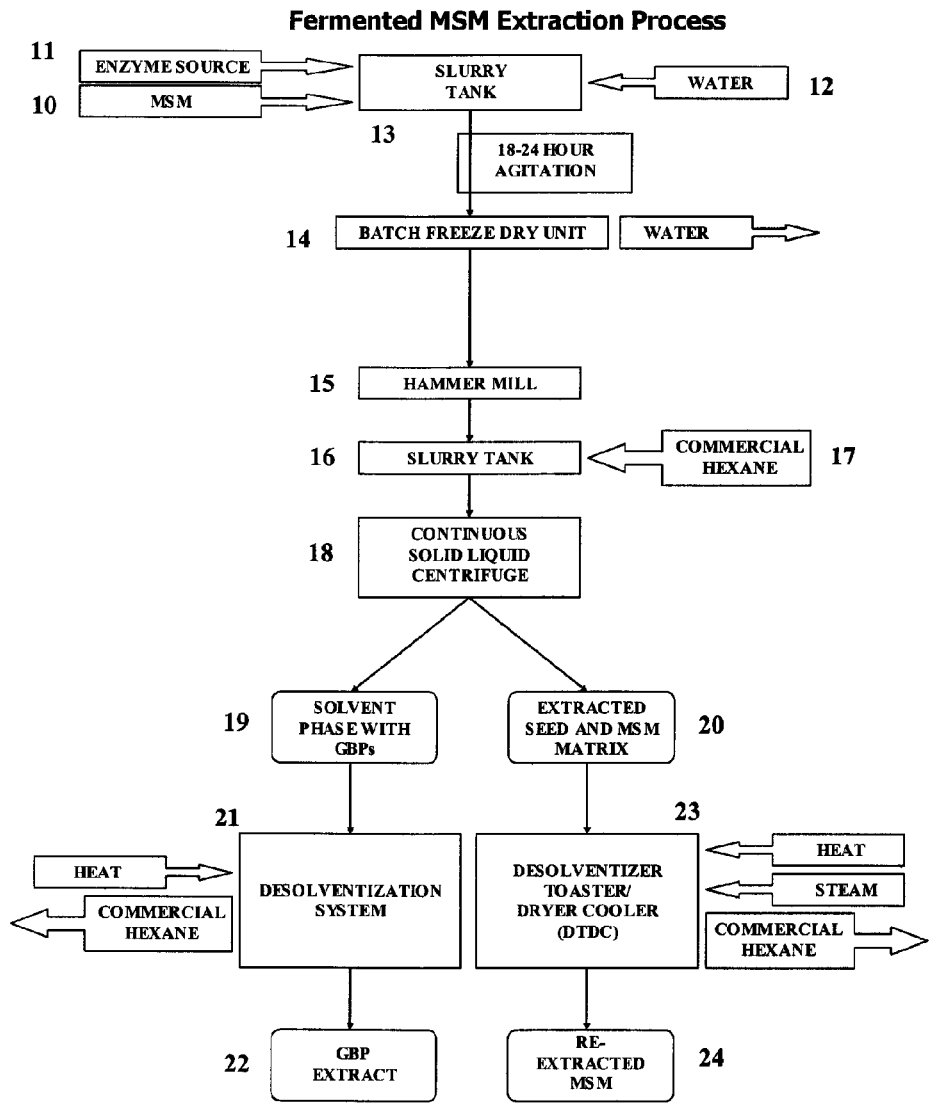
FIG. 14 shows, according to particular exemplary aspects, an exemplary process for 'fermenting' meadowfoam seedmeal (MSM) to produce glucosinolate breakdown products (GBPs), and for extracting the GBPs to provide for concentrated extracts comprising GBPs.

FIG. 14 shows, according to particular exemplary aspects, an exemplary process for 'fermenting' meadowfoam seedmeal (MSM) to produce glucosinolate breakdown products (GBPs), and for extracting the GBPs to provide for concentrated extracts comprising GBPs. With reference to FIG. 14, MSM 10, ground fresh meadowfoam seed 11, and water 12 are added to a slurry tank 13 in a ratio of 1:0.01:3. Sufficient agitation is provided to ensure the liquid is evenly distributed through the solids matrix. After agitating for 18-24 hours at a temperature of approximately 22° C. (e.g., 72° F.), the 'fermented' mixture is conveyed to a batch freeze drying unit 14 in which the moisture is stripped away. The dehydrated seed and 'fermented MSM material is then passed through a hammer mill 15 to break up any agglomerates and increase available surface area for extraction.

The milled seed and MSM matrix is then loaded into an explosion proof slurry tank 16 with commercial hexane 17. The ratio of hexane to seed (w/w) is between about 0.7:1 and 1:1. The temperature of the slurry is raised to approximately 54° C. (e.g., 130° F.) and agitation is maintained for at least 30 minutes.

After a minimum contact time between solvent 17 and seed/MSM matrix is achieved, the exit valve of the explosion proof slurry tank is opened, and the mixture is pumped to a continuous solid liquid centrifuge (separator) 18 (e.g., make by Westfalia, Oelde, Germany). The centrifuge 18 separates the solvent phase 19, now enriched in GBPs, from the spent seed and MSM matrix 20. The solvent phase 19 is passed through a solvent recovery system 21 and the hexane is removed, leaving the finished GBP extract 22. The extracted seed and MSM matrix 20 is conveyed to a DTDC 23 and the hexane is removed to produce a re-extracted MSM product 24, which is depleated of both oil and GBPs.

REFERENCES CITED (1) Vaughn, S. F.; Palmquist, D. E.; Duval, S. M.; Berhow, M. A., Herbicidal activity of glucosinolate-containing seedmeals. *Weed Science* 2006, 54, 743-748.

(2) Mason, C. T. *A systematic study of the genus Limnanthes*; University of California: Berkeley, 1952; pp 455-512.

(3) Jain, S. K. In *Domestication of Limnanthes (Meadowfoam) as a new oil crop.*, Plant domestication induced mutation: Proceedings of an advisory group meeting on the possible use of mutation breeding for rapid domestication of new crop plants, Vienna, Austria, 1986; Vienna, Austria, 1986; pp 121-134.

(4) Knapp, S. J.; Crane, J. M., Breeding advances and germplasm resources in meadowfoam: a very long chain oilseed. In *Perspectives on new crops and new uses*, Janick, J., Ed. ASHS Press: Alexandria, Va., 1999; pp 225-233.

(5) Miller, R. W.; Daxenbichler, M. E.; Earle, F. R., Search for new industrial oils, VIII. The genus *Limnanthes*. *J. Am. Oil Chem. Soc.* 1964, 41, 167-196.

(6) Ettlinger, M. G.; Lundeen, A. J., The mustard oil of Limnanthes douglasii seed, m-methoxybenzylisothiocyanate. *J. Am. Chem. Soc.* 1956, 78, 1952-1954.

(7) Vaughn, S. F.; Boydston, R. A.; Mallory-Smith, C. A., Isolation and identification of (3-methoxyphenyl)acetonitrile as a phytotoxin from meadowfoam (Limnanthes alba) seedmeal. *Journal of Chemical Ecology* 1996, 22, (10), 1939-1949.

(8) Hasapis, X.; MacLeod, A. J., Benzylglucosinolate degradation in heat-treated *Lepdium sativum* seeds and detection of a thiocyanate-forming factor. *Phytochemistry* 1982, 21, 1009-1013.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for converting glucosinolate in a glucosinolate-containing plant material to glucosinolate breakdown products (GBPs), comprising:
    providing an amount of processed glucosinolate-containing plant material, the processed plant material being depleted of oil and glucosinolate converting enzyme activity by virtue of said processing;
    providing an amount of exogenous glucosinolate converting enzyme activity comprising a thioglucosidase;
    contacting or mixing the processed glucosinolate-containing plant material with the amount of exogenous glucosinolate converting enzyme activity comprising the thioglucosidase to provide a mixture;
    hydrating the mixture; and
    incubating the hydrated mixture, wherein the glucosinolates in the processed glucosinolate-containing plant material are enzymatically converted to glucosinolate breakdown products (GBPs) by the exogenously provided glucosinolate converting enzyme activity comprising the thioglucosidase.

2. The method of claim 1, wherein the processed glucosinolate-containing plant material comprises a oilseed-derived seedmeal material from which the oil has been removed by the processing, and wherein the processing comprises at least one of solvent extraction and heat treatment.

3. The method of claim 1, wherein the exogenous glucosinolate converting enzyme activity comprises at least one of a myrosinase activity and a nitrile-forming activity.

4. The method of claim 1, wherein the exogenous glucosinolate converting enzyme activity comprises that of a heterologous plant relative to the processed glucosinolate-containing plant material.

5. The method of claim 1, wherein providing the exogenous glucosinolate converting enzyme activity comprises providing a plant material having glucosinolate converting enzyme activity.

6. The method of claim 5, wherein the plant material having glucosinolate converting enzyme activity comprises seed material of a seed oil plant.

7. The method of claim 6, wherein amount of plant material having glucosinolate converting enzyme activity is present in an amount less than 2 wt %, less than 5 wt %, or less than 10 wt %, relative to the amount of processed glucosinolate-containing plant material.

8. The method of claim 1, wherein the glucosinolate breakdown products (GBPs), comprise at least one product selected from the group consisting of a glucosinolate-derived isothiocyanate, a glucosinolate-derived nitrile and an acetamide derivative of a glucosinolate-derived nitrile.

9. The method of claim 8, wherein incubating the hydrated mixture is in the presence of an enzymatic co-factor or agent that promotes formation of the glucosinolate-derived nitrile or acetamide derivative of a glucosinolate-derived nitrile, relative to formation of the glucosinolate-derived isothiocyante.

10. The method of claim 9, wherein the enzymatic co-factor or agent comprises a metal ion.

11. The method of claim 10, wherein the metal is at least one selected from the group consisting of $Fe^{2+}$, $Zn^{2+}$, $Ca^{2+}$, $Mg^{2+}$, $Cu^{2+}$, and $Mn^{2+}$.

12. The method of claim 1, further comprising drying or freeze drying the incubated hydrated mixture.

13. The method of claim 1, wherein at least one of the processed glucosinolate-containing plant material and the exogenous glucosinolate converting enzyme activity comprises material from at least one plant selected from the group consisting of: Crambe (*Crambe abysinnica*); Black Mustard; Yellow Mustard (*Sinapis alba*); Oriental Mustard (*Brassica juncea*); Broccoli (*Brassica oleracea italica*); Rapeseed (*Brassica napus*); Meadowfoam (*Limnanthes alba*), Radish (*Raphanus sativus*); Wasabi (*Wasabia japonica*); Horseradish (*Cochlearia Armoracia*); Cauliflower; Garden cress (*Lepidium sativum*); Watercress (*Nasturtium officinalis*); and Papaya (*Carica papaya*).

14. The method of claim 13, wherein at least one of the processed glucosinolate-containing plant material and the exogenous glucosinolate converting enzyme activity comprises material from Meadowfoam (*Limnanthes alba*).

15. The method of claim 1, wherein at least one of the processed glucosinolate-containing plant material and the exogenous glucosinolate converting enzyme activity comprises material from the genus *Brassicas*.

16. A method for providing a low-fat composition comprising glucosinolate breakdown products (GBPs) derived from a glucosinolate-containing plant material, comprising:
providing an amount of processed glucosinolate-containing plant material, the processed plant material being depleted of oil and glucosinolate converting enzyme activity by virtue of said processing;
providing an amount of exogenous glucosinolate converting enzyme activity comprising a thioglucosidase;
contacting or mixing the processed glucosinolate-containing plant material with the amount of exogenous glucosinolate converting enzyme activity comprising the thioglucosidase to provide a mixture;
hydrating the mixture; and
incubating the hydrated mixture, wherein the glucosinolates in the processed glucosinolate-containing plant material are enzymatically converted to glucosinolate breakdown products (GBPs) by the exogenously provided glucosinolate converting enzyme activity comprising the thioglucosidase to provide for a low-fat composition comprising glucosinolate breakdown products (GBPs) derived from a glucosinolate-containing plant material.

17. The method of claim 16, further comprising drying or freeze drying the incubated hydrated mixture to provide for a dried composition comprising glucosinolate breakdown products (GBPs).

18. The method of claim 16, further comprising grinding, crushing, pulverizing, mincing, milling or otherwise breaking up the dried or freeze dried material to provide a dried or freeze dried material having increased surface area.

19. The method of claim 18, further comprising extracting the dried or freeze dried material having increased surface area with a suitable solvent to provide for partitioning of one or more glucosinolate breakdown products (GBPs) from the extracted dried or freeze dried material into the solvent.

20. The method of claim 19, further comprising segregating the extract-bearing solvent from the extracted dried or freeze dried material, and desolventizing the extract-bearing solvent to provide an extract composition comprising glucosinolate breakdown products (GBPs).

21. The method of claim 20, further comprising desolventizing the extracted dried or freeze dried material to provide a re-extracted plant material depleted of oil, glucosinolates and glucosinolate breakdown products (GBPs).

22. The method of claim 16, wherein the processed glucosinolate-containing plant material comprises a oilseed-derived seedmeal material from which the oil has been removed by the processing, and wherein the processing comprises at least one of solvent extraction and heat treatment.

23. The method of claim 16, wherein the low-fat composition comprises a glucosinolate breakdown product (GBP) to fat (free fatty acid (FFA) plus triacylglycerol (TAG)) ratio, in terms of wt %, in the range of about 1:1 to about 1:3.

24. The method of claim 20, wherein the extract composition comprises a glucosinolate breakdown product (GBP) to fat (free fatty acid (FFA) plus triacylglycerol (TAG)) ratio, in terms of wt %, in the range of about 1:1 to about 1:3.

25. The method of claim 16, wherein the exogenous glucosinolate converting enzyme activity comprises at least one of a myrosinase activity and a nitrile-forming activity.

26. The method of claim 16, wherein the exogenous glucosinolate converting enzyme activity comprises that of a heterologous plant relative to the processed glucosinolate-containing plant material.

27. The method of claim 16, wherein providing the exogenous glucosinolate converting enzyme activity comprises providing a plant material having glucosinolate converting enzyme activity.

28. The method of claim 27, wherein the plant material having glucosinolate converting enzyme activity comprises seed material of a seed oil plant.

29. The method of claim 28, wherein the amount of plant material having glucosinolate converting enzyme activity is present in an amount less than 2 wt %, less than 5 wt %, or less than 10 wt %, relative to the amount of processed glucosinolate-containing plant material.

30. The method of claim 16, wherein the glucosinolate breakdown products (GBPs) comprise at least one product selected from the group consisting of a glucosinolate-derived isothiocyante, a glucosinolate-derived nitrile and an acetamide derivative of a glucosinolate-derived nitrile.

31. The method of claim 30, wherein incubating the hydrated mixture is in the presence of an enzymatic co-factor or agent that promotes formation of the glucosinolate-derived nitrile or acetamide derivative of a glucosinolate-derived nitrile, relative to formation of the glucosinolate-derived isothiocyante.

32. The method of claim 31, wherein the enzymatic co-factor or agent comprises a metal ion.

33. The method of claim 32, wherein the metal is at least one selected from the group consisting of $Fe^{2+}$, $Zn^{2+}$, $Ca^{2+}$, $Mg^{2+}$, $CU^{2+}$, and $Mn^{2+}$.

34. The method claim 16, wherein at least one of the processed glucosinolate-containing plant material and the exogenous glucosinolate converting enzyme activity comprises material from at least one plant selected from the group consisting of: Crambe (*Crambe abysinnica*); Black Mustard; Yellow Mustard (*Sinapis alba*); Oriental Mustard (*Brassica juncea*); Broccoli (*Brassica oleracea italica*); Rapeseed (*Brassica napus*); Meadowfoam (*Limnanthes alba*), Radish (*Raphanus sativus*); Wasabi (*Wasabia japonica*); Horseradish (*Cochlearia Armoracia*); Cauliflower; Garden cress (*Lepidium sativum*); Watercress (*Nasturtium officinalis*); and Papaya (*Carica papaya*).

35. The method of claim 34, wherein at least one of the processed glucosinolate-containing plant material and the exogenous glucosinolate converting enzyme activity comprises material from Meadowfoam (*Limnanthes alba*).

36. The method of claim 16, wherein at least one of the processed glucosinolate-containing plant material and the exogenous glucosinolate converting enzyme activity comprises material from the genus *Brassicas*.

37. A method for providing a low-fat composition comprising a glucosinolate-containing plant material, comprising:
providing an amount of processed glucosinolate-containing plant material, the processed plant material being depleted of oil and glucosinolate converting enzyme activity by virtue of said processing;
providing an amount of exogenous glucosinolate converting enzyme activity comprising a thioglucosidase; and
mixing the processed glucosinolate-containing plant material with the amount of exogenous glucosinolate converting enzyme activity comprising the thioglucosidase to provide a low-fat composition comprising a processed glucosinolate-containing plant material.

38. The method of claim 37, further comprising drying or freeze drying the low-fat composition to provide for a dried low-fat composition comprising glucosinolate breakdown products (GBPs).

39. The method of claim 37, further comprising grinding, crushing, pulverizing, mincing, milling or otherwise breaking up the dried or freeze dried material to provide a dried or freeze dried low-fat material having increased surface area.

40. The method of claim 37, further comprising pelletizing, compressing, or otherwise consolidating the low-fat composition comprising a glucosinolate-containing plant material.

41. The method of claim 37, wherein the processed glucosinolate-containing plant material comprises a oilseed-derived seedmeal material from which the oil has been removed by the processing, and wherein the processing comprises at least one of solvent extraction and heat treatment.

42. The method of claim 37, wherein the exogenous glucosinolate converting enzyme activity comprises at least one of a myrosinase activity and a nitrile-forming activity.

43. The method of claim 37, wherein the exogenous glucosinolate converting enzyme activity comprises that of a heterologous plant relative to the processed glucosinolate-containing plant material.

44. The method of claim 37, wherein providing the exogenous glucosinolate converting enzyme activity comprises providing a plant material having glucosinolate converting enzyme activity.

45. The method of claim 44, wherein the plant material having glucosinolate converting enzyme activity comprises seed material of a seed oil plant.

46. The method of claim 45, wherein amount of plant material having glucosinolate converting enzyme activity is present in an amount less than 2 wt %, less than 5 wt %, or less than 10 wt %, relative to the amount of processed glucosinolate-containing plant material.

47. The method of claim 37, wherein the glucosinolate breakdown products (GBPs), comprise at least one product selected from the group consisting of a glucosinolate-derived isothiocyante, a glucosinolate-derived nitrile and an acetamide derivative of a glucosinolate-derived nitrile.

48. The method of claim 37, further comprising providing an enzymatic co-factor or agent that promotes formation of the glucosinolate-derived nitrile or acetamide derivative of a glucosinolate-derived nitrile, relative to formation of the glucosinolate-derived isothiocyante, and mixing the enzymatic co-factor or agent with the processed glucosinolate-containing plant material and the glucosinolate converting enzyme activity.

49. The method of claim 48, wherein the enzymatic co-factor or agent comprises a metal ion.

50. The method of claim 49, wherein the metal is at least one selected from the group consisting of $Fe^{2+}$, $Zn^{2+}$, $Ca^{2+}$, $Mg^{2+}$, $Cu^{2+}$, and $Mn^{2+}$.

51. The method of claim 37, wherein at least one of the processed glucosinolate-containing plant material and the exogenous glucosinolate converting enzyme activity comprises material from at least one plant selected from the group consisting of: Crambe (*Crambe abysinnica*); Black Mustard; Yellow Mustard (*Sinapis alba*); Oriental Mustard (*Brassica juncea*); Broccoli (*Brassica oleracea italica*); Rapeseed (*Brassica napus*); Meadowfoam (*Limnanthes alba*), Radish (*Raphanus sativus*); Wasabi (*Wasabia japonica*); Horseradish (*Cochlearia Armoracia*); Cauliflower; Garden cress (*Lepidium sativum*); Watercress (*Nasturtium officinalis*); and Papaya (*Carica papaya*).

52. The method of claim 51, wherein at least one of the processed glucosinolate-containing plant material and the exogenous glucosinolate converting enzyme activity comprises material from Meadowfoam (*Limnanthes alba*).

53. The method of claim 37, wherein at least one of the processed glucosinolate-containing plant material and the exogenous glucosinolate converting enzyme activity comprises material from the genus *Brassicas*.

* * * * *